(12) United States Patent
Orbay et al.

(10) Patent No.: US 7,927,341 B2
(45) Date of Patent: Apr. 19, 2011

(54) NAIL PLATE AND JIG THEREFOR

(75) Inventors: Jorge L. Orbay, Coral Gables, FL (US);
Javier E. Castaneda, Miami, FL (US);
Marcus Bourda, Miami, FL (US);
Cesare Cavallazzi, Miramar, FL (US);
Robert Graham, Miami, FL (US); Eric Feliciano, Tampa, FL (US)

(73) Assignee: Depuy Products, Inc., Warsaw, IN (US)

( * ) Notice: Subject to any disclaimer, the term of this patent is extended or adjusted under 35 U.S.C. 154(b) by 1415 days.

(21) Appl. No.: 11/277,160

(22) Filed: Mar. 22, 2006

(65) Prior Publication Data

US 2006/0200157 A1     Sep. 7, 2006

Related U.S. Application Data

(63) Continuation-in-part of application No. 11/341,248, filed on Jan. 26, 2006.

(60) Provisional application No. 60/648,989, filed on Jan. 28, 2005.

(51) Int. Cl.
*A61B 17/58* (2006.01)
*A61B 17/60* (2006.01)
*A61F 2/00* (2006.01)

(52) U.S. Cl. .............. 606/104; 606/62; 606/96; 606/98; 606/99

(58) Field of Classification Search ............ 606/62, 606/64, 96–98
See application file for complete search history.

(56) References Cited

U.S. PATENT DOCUMENTS

| | | |
|---|---|---|
| 1,091,674 A | 3/1914 | Lee |
| 2,077,804 A | 4/1937 | Morrison |
| 2,500,370 A | 6/1947 | McKibbin |
| 2,685,877 A | 8/1954 | Dobelle |
| 2,821,979 A | 2/1958 | Cameron |
| 3,025,853 A | 3/1962 | Mason |
| 3,236,141 A | 2/1966 | Smith |
| 3,489,143 A | 1/1970 | Halloran |
| 3,552,389 A | 1/1971 | Allgower et al. |
| 3,668,972 A | 6/1972 | Allgower et al. |
| 3,716,050 A | 2/1973 | Johnston |

(Continued)

FOREIGN PATENT DOCUMENTS

CH      611147      5/1979

(Continued)

OTHER PUBLICATIONS

Philos, The Anatomical Fixation Sytem for the Proximal Humerus with Angular Stability, XP-002205191, Jan. 1, 2001, pp. 1-3.

(Continued)

*Primary Examiner* — Thomas C Barrett
*Assistant Examiner* — Andrew Yang
(74) *Attorney, Agent, or Firm* — Gordon & Jacobson, PC

(57) ABSTRACT

A humeral fracture fixation system is provided and includes a nail-plate fixation device having a plate-like head portion, an intramedullary nail portion, and a bent neck portion therebetween which creates an angle between the plate and nail portions. The upper surface of the nail portion is substantially straight for contact with the endosteum and the nail portion includes threaded holes for machine screws. The head portion includes locking holes for receiving fixed-angle bone support elements, and K-wire alignment holes. The front of the head portion includes suture holes while presenting a smooth profile. A specific implantation jigs and a screw guide cannula are also provided.

13 Claims, 23 Drawing Sheets

U.S. PATENT DOCUMENTS

| | | | |
|---|---|---|---|
| 3,779,240 A | 12/1973 | Kondo | |
| 3,791,380 A | 2/1974 | Dawidowski | |
| 3,939,498 A | 2/1976 | Lee et al. | |
| RE28,841 E | 6/1976 | Allgower et al. | |
| 4,135,507 A | 1/1979 | Harris | |
| 4,153,953 A | 5/1979 | Grobbelaar | |
| 4,172,452 A | 10/1979 | Forte et al. | |
| 4,219,015 A | 8/1980 | Steinemann | |
| 4,408,601 A | 10/1983 | Wenk | |
| RE31,628 E | 7/1984 | Allgower et al. | |
| 4,465,065 A * | 8/1984 | Gotfried | 606/65 |
| 4,483,335 A | 11/1984 | Tornier | |
| 4,493,317 A | 1/1985 | Klaue | |
| 4,498,468 A | 2/1985 | Hansson | |
| 4,506,662 A | 3/1985 | Anapliotis | |
| 4,513,744 A | 4/1985 | Klaue | |
| 4,561,432 A | 12/1985 | Mazor | |
| 4,565,193 A | 1/1986 | Streli | |
| 4,622,959 A | 11/1986 | Marcus | |
| 4,632,101 A | 12/1986 | Freedland | |
| 4,721,103 A | 1/1988 | Freedland | |
| 4,733,654 A | 3/1988 | Marino | |
| 4,776,330 A | 10/1988 | Chapman et al. | |
| 4,794,919 A | 1/1989 | Nilsson | |
| 4,838,252 A | 6/1989 | Klaue | |
| 4,858,602 A | 8/1989 | Seidel et al. | |
| 4,923,471 A | 5/1990 | Morgan | |
| 4,927,421 A | 5/1990 | Goble et al. | |
| 4,957,118 A | 9/1990 | Erlebacher | |
| 4,957,497 A | 9/1990 | Hoogland et al. | |
| 4,988,350 A | 1/1991 | Herzberg | |
| 5,002,544 A | 3/1991 | Klaue et al. | |
| 5,006,120 A | 4/1991 | Carter | |
| 5,013,314 A | 5/1991 | Firica et al. | |
| 5,035,697 A | 7/1991 | Frigg | |
| 5,041,114 A | 8/1991 | Chapman et al. | |
| 5,085,660 A | 2/1992 | Lin | |
| 5,127,914 A | 7/1992 | Calderale et al. | |
| 5,129,901 A | 7/1992 | Decoste | |
| 5,151,103 A | 9/1992 | Tepic et al. | |
| 5,160,335 A | 11/1992 | Wagenknecht | |
| 5,180,383 A | 1/1993 | Haydon | |
| 5,190,544 A | 3/1993 | Chapman et al. | |
| 5,197,966 A | 3/1993 | Sommerkamp | |
| 5,269,784 A | 12/1993 | Mast | |
| 5,275,601 A | 1/1994 | Gogolewski et al. | |
| 5,304,180 A | 4/1994 | Slocum | |
| 5,324,290 A | 6/1994 | Zdeblick et al. | |
| 5,324,291 A | 6/1994 | Ries et al. | |
| 5,352,229 A | 10/1994 | Goble et al. | |
| 5,356,410 A | 10/1994 | Pennig | |
| 5,364,398 A | 11/1994 | Chapman et al. | |
| 5,364,399 A | 11/1994 | Lowery et al. | |
| 5,366,457 A | 11/1994 | McGuire et al. | |
| 5,382,248 A | 1/1995 | Jacobson et al. | |
| 5,429,641 A | 7/1995 | Gotfried | |
| 5,458,654 A | 10/1995 | Tepic | |
| 5,472,444 A | 12/1995 | Huebner et al. | |
| 5,484,438 A | 1/1996 | Pennig | |
| 5,489,284 A | 2/1996 | James et al. | |
| 5,514,138 A | 5/1996 | McCarthy | |
| 5,531,748 A | 7/1996 | de la Caffiniere | |
| 5,536,127 A | 7/1996 | Pennig | |
| 5,578,035 A | 11/1996 | Lin | |
| 5,591,168 A | 1/1997 | Judet et al. | |
| 5,601,553 A | 2/1997 | Trebing et al. | |
| 5,603,715 A | 2/1997 | Kesler | |
| 5,658,283 A | 8/1997 | Huebner | |
| 5,662,655 A | 9/1997 | Laboureau et al. | |
| 5,665,087 A | 9/1997 | Huebner | |
| 5,674,222 A | 10/1997 | Berger et al. | |
| 5,676,667 A | 10/1997 | Hausman | |
| 5,702,399 A | 12/1997 | Kilpela et al. | |
| 5,709,682 A | 1/1998 | Medoff | |
| 5,709,686 A | 1/1998 | Talos et al. | |
| 5,718,705 A | 2/1998 | Sammarco | |
| 5,728,099 A | 3/1998 | Tellman et al. | |
| 5,749,872 A | 5/1998 | Kyle et al. | |
| 5,759,184 A | 6/1998 | Santangelo | |
| 5,766,174 A | 6/1998 | Perry | |
| 5,776,194 A | 7/1998 | Mikol et al. | |
| 5,797,913 A | 8/1998 | Dambreville et al. | |
| 5,810,823 A | 9/1998 | Klaue et al. | |
| 5,840,078 A | 11/1998 | Yerys | |
| 5,843,127 A | 12/1998 | Li | |
| 5,849,004 A | 12/1998 | Bramlet | |
| 5,853,415 A | 12/1998 | Bertin et al. | |
| 5,882,351 A | 3/1999 | Fox | |
| 5,897,557 A * | 4/1999 | Chin et al. | 606/71 |
| 5,928,234 A | 7/1999 | Manspeizer | |
| 5,931,839 A | 8/1999 | Medoff | |
| 5,938,664 A | 8/1999 | Winquist et al. | |
| 5,976,139 A | 11/1999 | Bramlet | |
| 5,993,449 A | 11/1999 | Schlapfer et al. | |
| 6,096,040 A | 8/2000 | Esser | |
| 6,139,552 A | 10/2000 | Horiuchi | |
| 6,146,384 A | 11/2000 | Lee et al. | |
| 6,183,474 B1 | 2/2001 | Bramlet et al. | |
| 6,183,475 B1 | 2/2001 | Lester et al. | |
| 6,206,881 B1 | 3/2001 | Frigg et al. | |
| D443,060 S | 5/2001 | Benirschke et al. | |
| 6,238,395 B1 | 5/2001 | Bonutti | |
| 6,270,499 B1 | 8/2001 | Leu et al. | |
| 6,287,310 B1 | 9/2001 | Fox | |
| 6,293,949 B1 | 9/2001 | Justis et al. | |
| 6,322,562 B1 | 11/2001 | Wolter | |
| 6,355,041 B1 | 3/2002 | Martin | |
| 6,358,250 B1 | 3/2002 | Orbay | |
| 6,364,882 B1 | 4/2002 | Orbay | |
| 6,379,359 B1 | 4/2002 | Dahners | |
| 6,406,477 B1 | 6/2002 | Fujiwara | |
| 6,409,768 B1 | 6/2002 | Tepic et al. | |
| 6,440,135 B2 | 8/2002 | Orbay et al. | |
| 6,443,954 B1 | 9/2002 | Bramlet et al. | |
| 6,454,770 B1 | 9/2002 | Klaue | |
| 6,468,278 B1 | 10/2002 | Muckter | |
| 6,514,253 B1 | 2/2003 | Yao | |
| 6,527,775 B1 | 3/2003 | Warburton | |
| 6,527,776 B1 | 3/2003 | Michelson | |
| 6,558,388 B1 | 5/2003 | Bartsch et al. | |
| 6,562,042 B2 | 5/2003 | Nelson | |
| 6,579,293 B1 | 6/2003 | Chandran | |
| 6,579,294 B2 | 6/2003 | Robioneck | |
| D479,331 S | 9/2003 | Pike et al. | |
| 6,623,486 B1 | 9/2003 | Weaver et al. | |
| 6,648,889 B2 | 11/2003 | Bramlet et al. | |
| 6,648,890 B2 | 11/2003 | Culbert et al. | |
| 6,669,701 B2 | 12/2003 | Steiner et al. | |
| 6,685,706 B2 | 2/2004 | Padget et al. | |
| 6,689,135 B2 | 2/2004 | Enayati | |
| 6,692,496 B1 | 2/2004 | Wardlaw | |
| 6,706,046 B2 | 3/2004 | Orbay et al. | |
| 6,730,090 B2 | 5/2004 | Orbay et al. | |
| 6,746,453 B2 | 6/2004 | Deloge et al. | |
| 6,866,665 B2 | 3/2005 | Orbay | |
| 6,926,720 B2 | 8/2005 | Castaneda | |
| 7,153,309 B2 * | 12/2006 | Huebner et al. | 606/96 |
| 7,425,213 B2 | 9/2008 | Orbay | |
| 7,588,577 B2 | 9/2009 | Fencl et al. | |
| 7,648,508 B2 * | 1/2010 | Lutz et al. | 606/86 R |
| 7,686,808 B2 | 3/2010 | Orbay et al. | |
| 7,722,611 B2 | 5/2010 | Cavallazzi et al. | |
| 2001/0011172 A1 | 8/2001 | Orbay et al. | |
| 2002/0049445 A1 | 4/2002 | Hall, IV et al. | |
| 2002/0058941 A1 | 5/2002 | Clark et al. | |
| 2002/0156474 A1 | 10/2002 | Wack et al. | |
| 2002/0161369 A1 | 10/2002 | Bramlet | |
| 2003/0004514 A1 | 1/2003 | Frigg et al. | |
| 2003/0055428 A1 | 3/2003 | Swanson | |
| 2003/0083661 A1 | 5/2003 | Orbay et al. | |
| 2003/0105461 A1 | 6/2003 | Putnam | |
| 2003/0216742 A1 | 11/2003 | Wetzler et al. | |
| 2004/0111090 A1 | 6/2004 | Dahners | |
| 2005/0010226 A1 | 1/2005 | Grady, Jr. et al. | |
| 2005/0021033 A1 | 1/2005 | Zeiler et al. | |
| 2005/0049594 A1 | 3/2005 | Wack et al. | |
| 2005/0065520 A1 | 3/2005 | Orbay | |

| | | | |
|---|---|---|---|
| 2005/0080421 A1 | 4/2005 | Weaver et al. | |
| 2005/0085818 A1 | 4/2005 | Huebner | |
| 2005/0182406 A1 | 8/2005 | Orbay et al. | |
| 2006/0015101 A1 | 1/2006 | Warburton et al. | |
| 2007/0173839 A1 | 7/2007 | Running et al. | |
| 2007/0173843 A1 | 7/2007 | Matityahu | |

FOREIGN PATENT DOCUMENTS

| | | |
|---|---|---|
| DE | 8907443 | 9/1989 |
| DE | G 92 00 328.1 | 4/1992 |
| DE | 43 41 980 A | 6/1995 |
| DE | 43 43 117 A1 | 6/1995 |
| DE | 44 38 264 A1 | 3/1996 |
| DE | 93 21 544 U1 | 10/1999 |
| DE | 19857279 | 6/2000 |
| DE | 29907161 | 8/2000 |
| DE | 20200705 U1 | 3/2002 |
| EP | 0165666 A1 | 12/1985 |
| EP | 0 207 884 A2 | 1/1987 |
| EP | 0737444 A1 | 10/1996 |
| EP | 1086655 A1 | 10/2001 |
| EP | 1 468 655 A2 | 10/2004 |
| FR | 2233973 | 1/1975 |
| FR | 2405062 | 5/1979 |
| FR | 2405705 | 5/1979 |
| FR | 2405706 | 5/1979 |
| FR | 2 606 268 | 5/1988 |
| JP | 04138152 | 5/1992 |
| SU | 1279626 | 12/1986 |
| WO | WO 97/09000 | 3/1997 |
| WO | WO 00/53110 | 9/2000 |
| WO | WO 00/53111 | 9/2000 |
| WO | WO 02/096309 A1 | 12/2002 |
| WO | WO2005037117 | 4/2005 |
| WO | WO2005053548 A1 | 6/2005 |

OTHER PUBLICATIONS

Hessman et al., "Internal Fixation of Proximal Humeral Fractures: Current Concepts," European Journal of Trauma, 2003 No. 5, p. 253-261.

Osgood and Ahmad, "Two- and Three-Part Fractures of the Proximal Humerus," Shoulder and Elbow Trauma, 2004, Chapter 13, p. 169-182.

Zimmer Periarticular Plating System- Low-Profile Fixation (catalog). Zimmer, Inc., 2003. (8 pages).

The Mayo Clinic Congruent Elbow Plates (catalog). ACUMED. Hillsboro, OR: 2003. (20 pages).

Locking Compression Plate (LCP) System (brochure). SYNTHES. West Chester, PA: 2003. (6 pages).

Two non-published pages of sketches made by Eduardo Gonzalez-Hernandez (initialed 'egh') in Miami, FL on Nov. 12, 2003, provided to inventor on that date.

(Disclosure by the inventor in the above pages has been redacted for clarity.).

Article: "The Hand Sourcebook" (Instruments for Surgeons) by K. Medic; dated 2002; 5 pgs.

Article SCS/D "Distal Radius Plate System"; Avanta Orthopaedics 1997; 6 pgs.

* cited by examiner

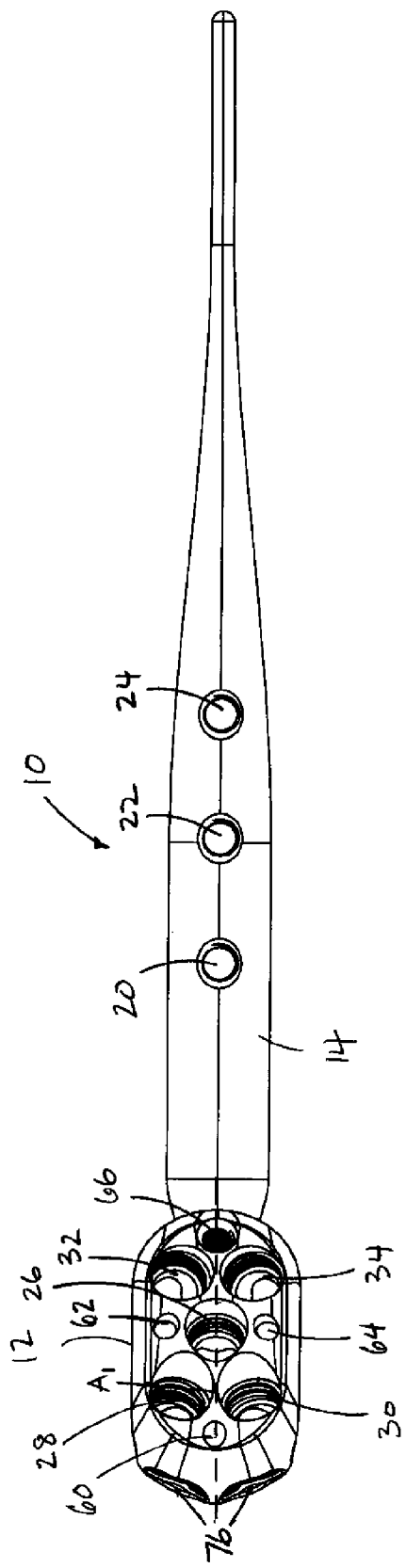
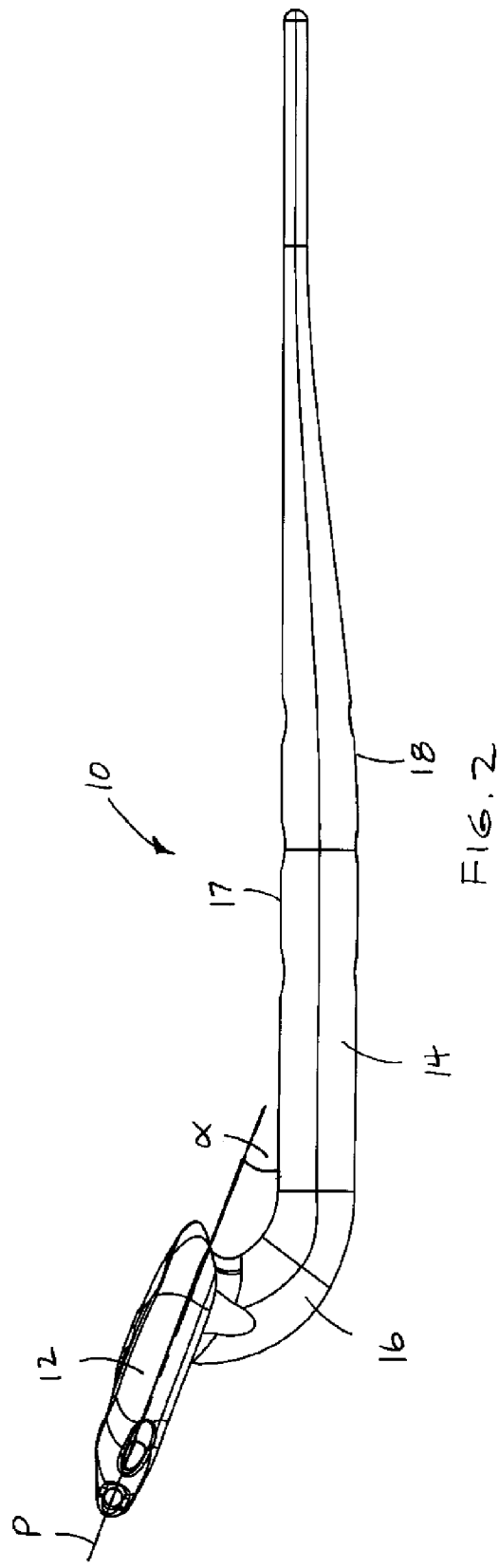

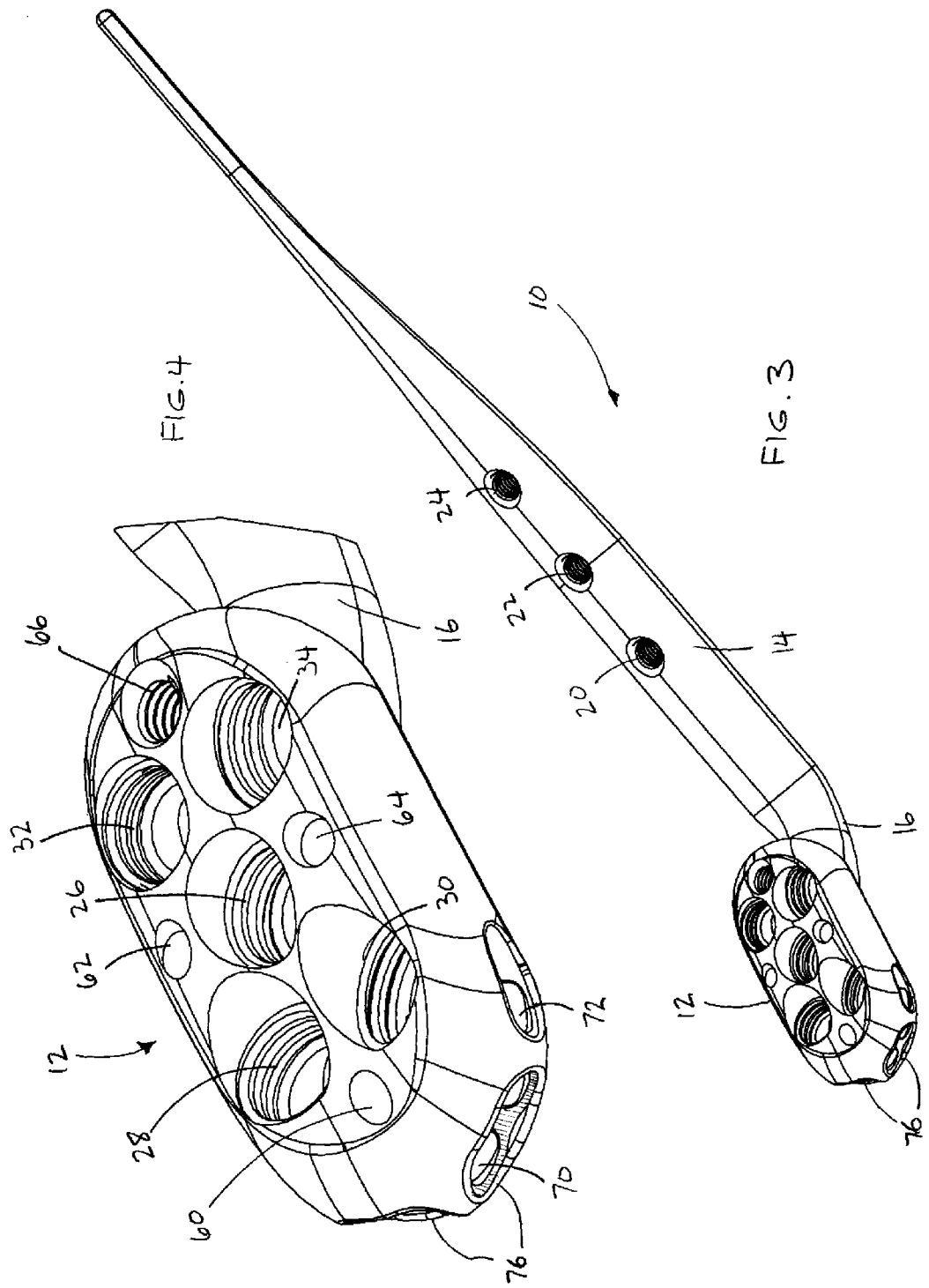

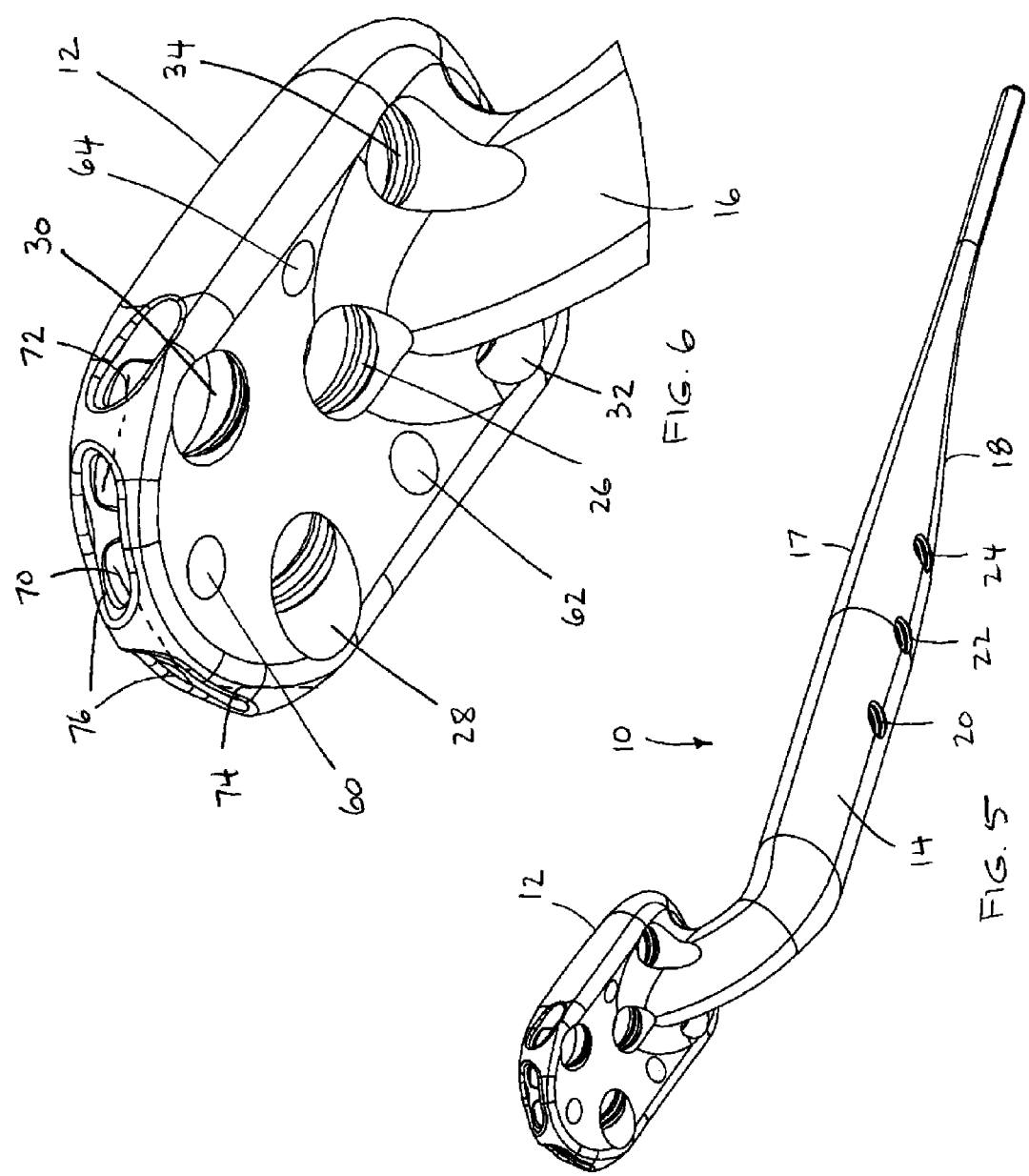

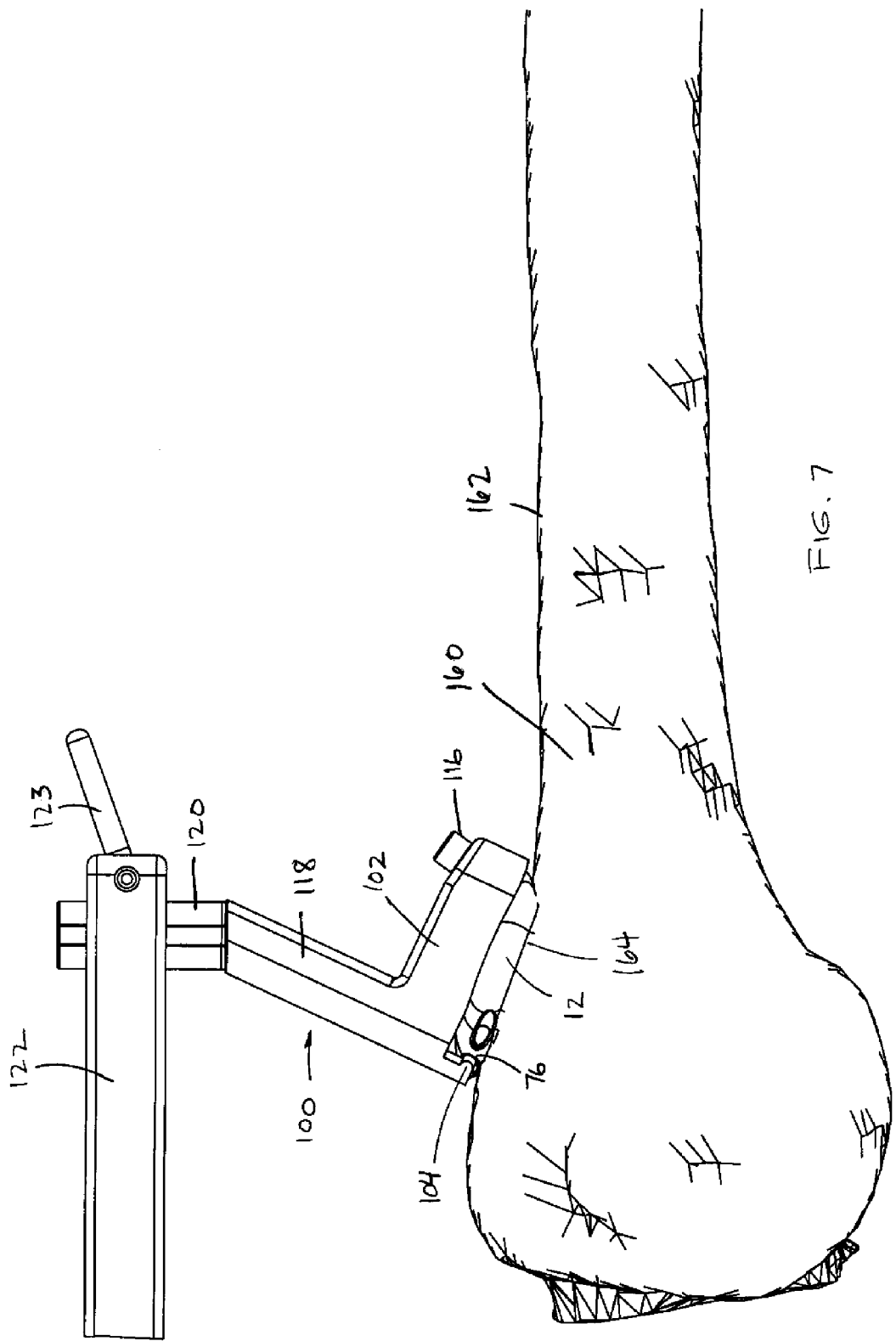

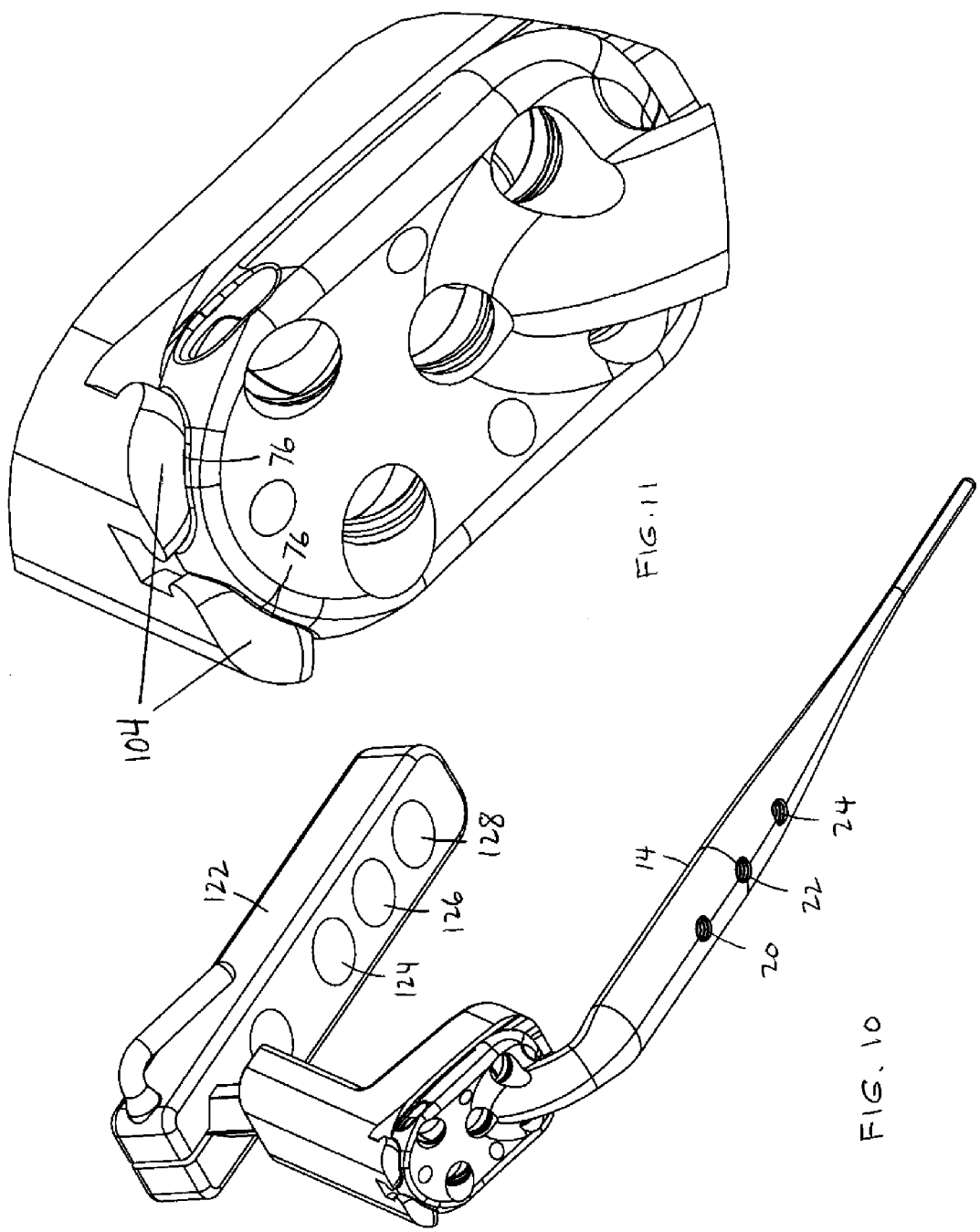

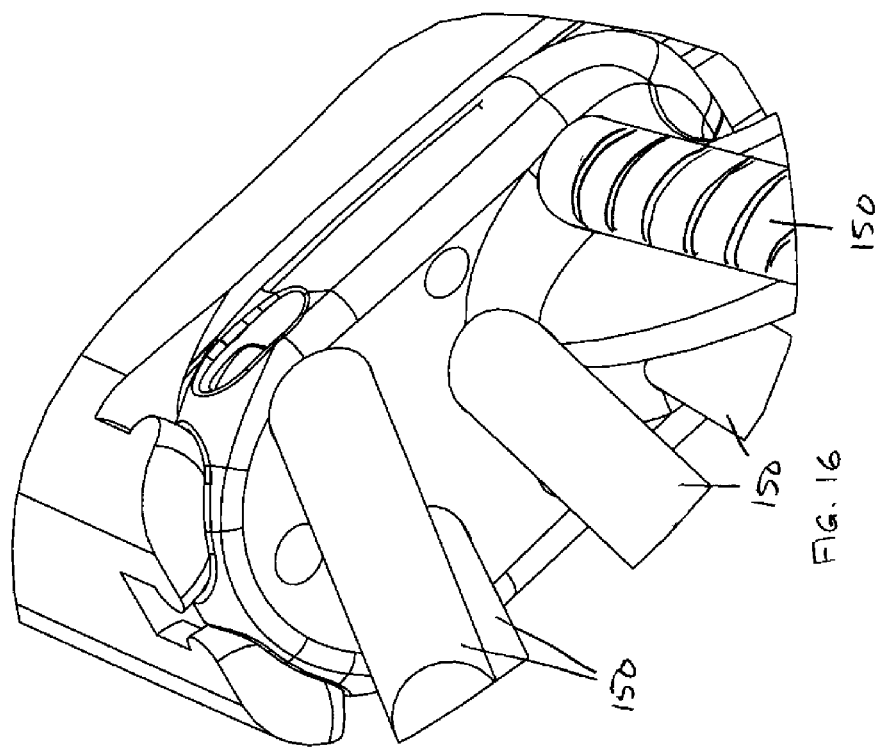
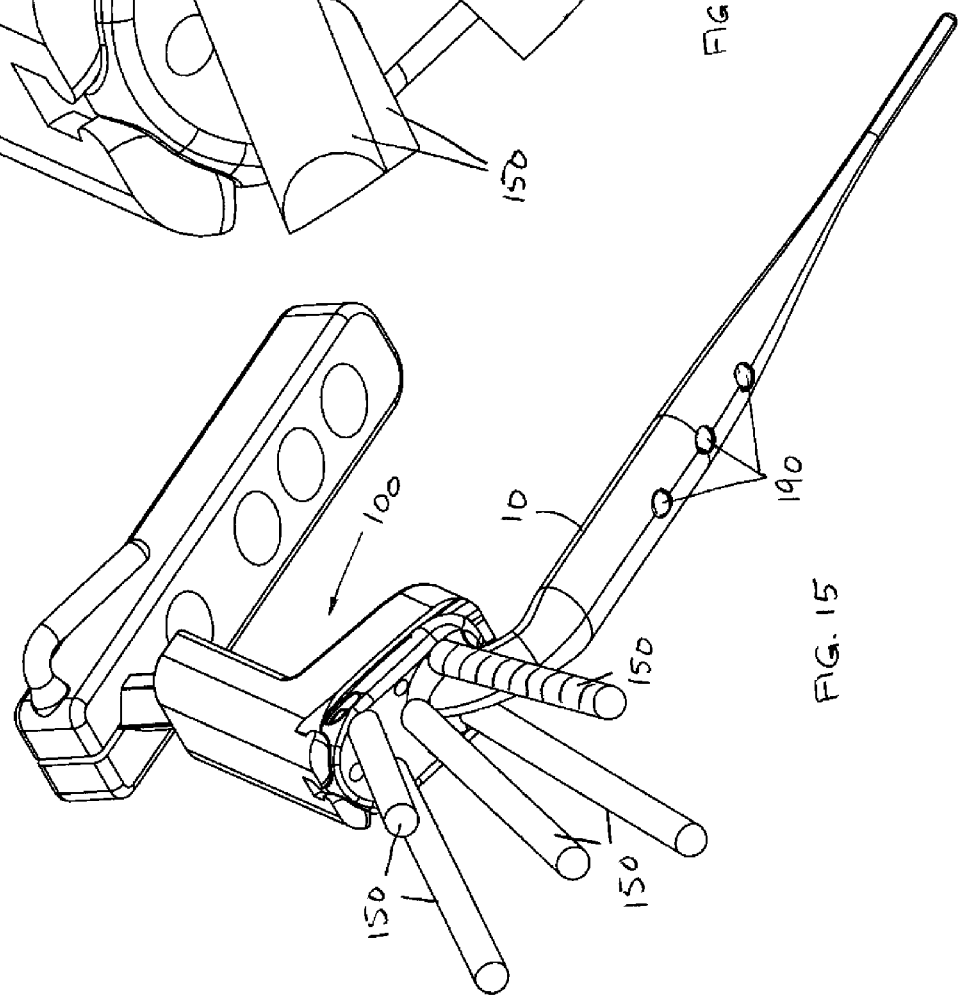

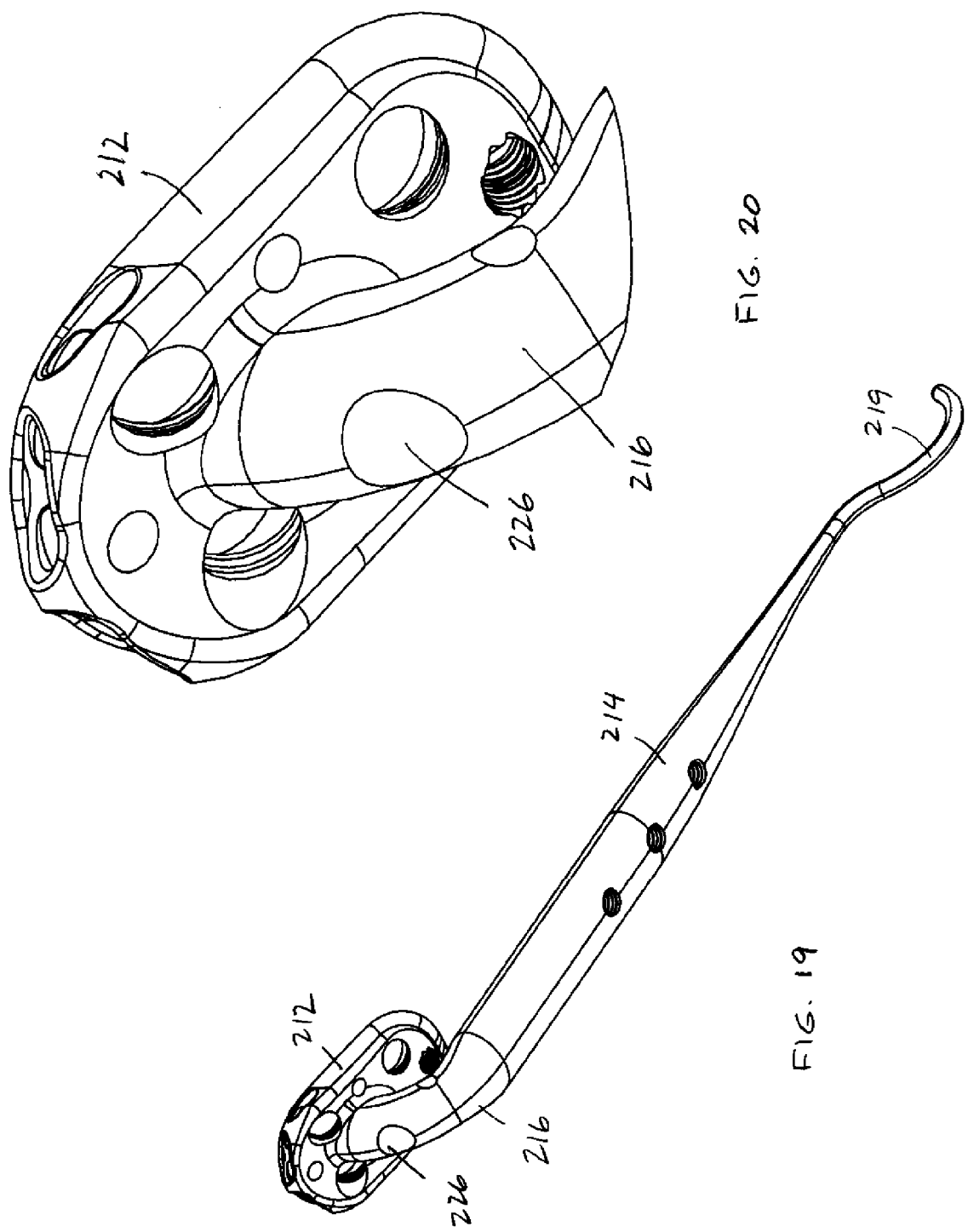

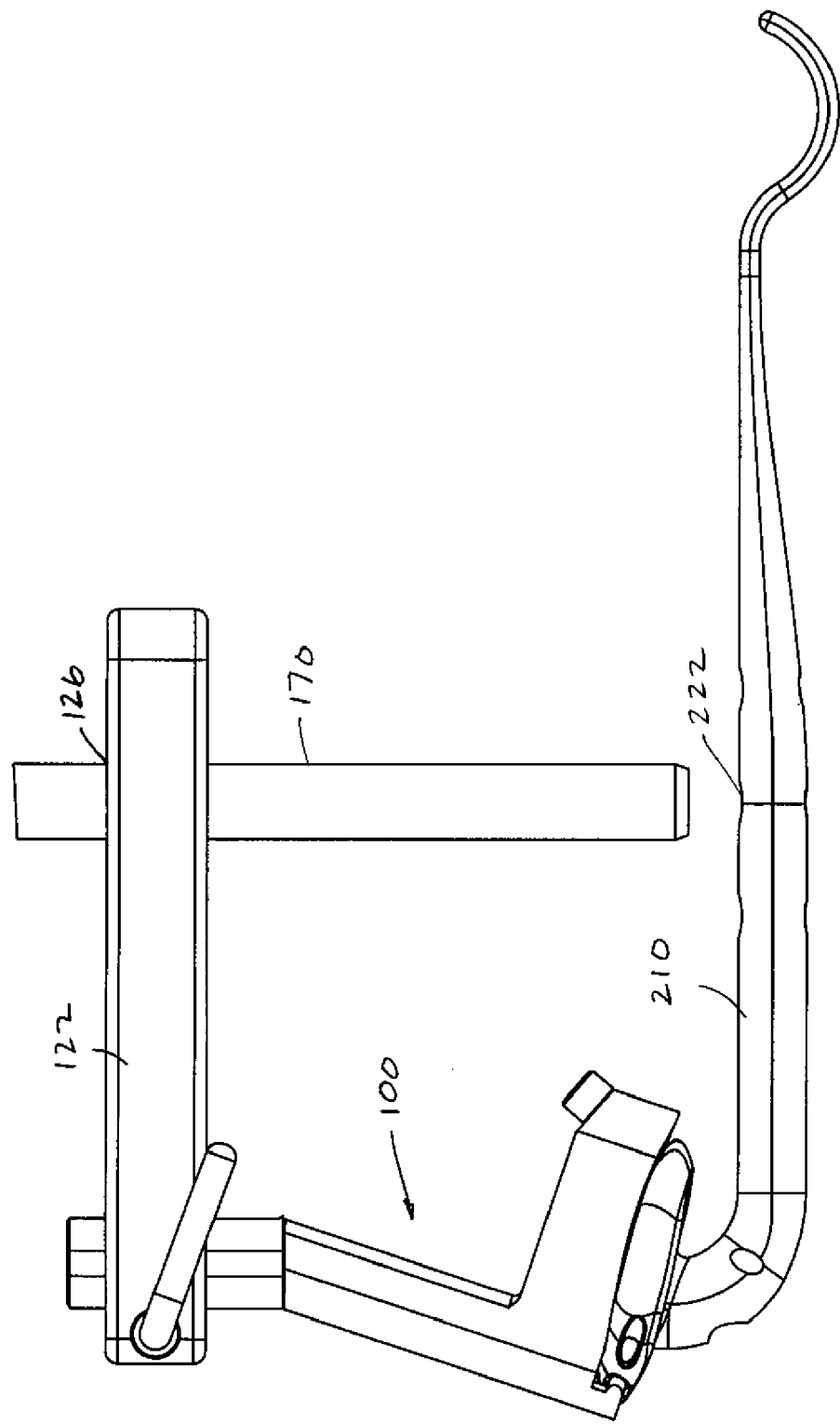

NAIL PLATE AND JIG THEREFOR

CROSS REFERENCE TO RELATED APPLICATIONS

This application is a continuation-in-part of U.S. Ser. No. 11/341,248, filed Jan. 26, 2006, which claims the benefit of U.S. Provisional Application No. 60/648,989, filed Jan. 28, 2005, both of which are hereby incorporated by reference herein in their entireties.

BACKGROUND OF THE INVENTION

1. Field of the Invention

This invention relates broadly to surgical devices. More particularly, this invention relates to an orthopedic fracture fixation system, and instrumentation for implanting the same.

2. State of the Art

The proximal humerus comprises the upper portion of the humerus, i.e. upper arm of the human body, commonly known as the shoulder area. Fractures of the proximal humerus typically result from traumatic injuries such as sporting accidents and can be more frequent with age due to reduction in bone density. Fractures of the proximal humerus are treated by exposing the fracture site, reducing the bone fracture, and then placing a plate over a relatively large area of the bone to immobilize the fracture in the reduced position for healing. Reducing the fracture includes realigning and positioning the fractured portions of the bone to their original position or similar stable position. Fixating the fracture includes positioning a plate over the fractured portions and securing the plate onto the fractured bones and adjacent non-fractured bones with bone screws.

Conventional fixation plates have several shortcomings when applied to the proximal humerus. In general, they are generally not well contoured for the humeral anatomy, and when provided in a size necessary to provide the structural rigidity for stability of a humeral fracture are not easily shaped by the surgeon. Furthermore, they require that a significant amount of tissue be exposed and displaced in order to position and secure the plate.

SUMMARY OF THE INVENTION

It is therefore an object of the invention to provide a humeral fracture fixation system which is anatomically appropriate for the humerus.

It is another object of the invention to provide a humeral fracture fixation system which provides a stable framework for support of a proximal humeral fracture.

It is a further object of the invention to provide a humeral fracture fixation system which does note require displacing a large amount of tissue.

It is also object of the invention to provide a humeral fracture fixation system which is relatively minimally invasive.

It is yet another object of the invention to provide a humeral fracture fixation system which facilitates alignment of the fixation device with the humeral shaft and fasteners with the head of the humerus.

It is still another object of the invention to provide a humeral fracture fixation system which is non-irritating to surrounding tissue.

It is still a further object of the invention to provide instrumentation for implanting a humeral fracture fixation system.

In accord with these objects, which will be discussed in detail below, a humeral fracture fixation system is provided and includes a nail-plate fixation device having a plate-like head portion, an intramedullary nail portion, and a bent neck portion therebetween which creates an angle between the plate and nail portions.

The upper surface of the nail portion is substantially straight, while a lower portion tapers in dimension. The nail portion includes cortical screw holes which preferably are provided with machine threads for receiving the threaded shaft of a screw with machine threads.

The head portion includes locking holes for receiving fixed-angle locking pegs or locking screws, and K-wire alignment holes. The front of the head portion includes suture holes. Preferably such suture holes are tunnel-like, accessible by a curved suture needle. In a preferred embodiment, three tunnels are provided: a first central tunnel perpendicular to a proximal-distal axis of the head portion and extending through the central plate of the head portion, and second and third tunnels on either side of the first which are at angle of about 45°±15° degrees with respect to the first tunnel. According to the invention, the upper and front contours of the head portion are devoid of scallops and protrusions and practically unaffected by the existence of the suture holes. The advantage of a smooth front end is that it presents no side-to-side resistance to tissue moving across the head portion.

An implantation jig is also provided which can be coupled to device, and specifically the head portion. The jig attaches to the head portion via a catch at the front end of the head portion nail plate and a locking screw. This catch is defined by two grooves in between the three suture holes at the front end of the plate. The grooves also allow a suture needle to enter the tunnels.

The handle of the jig can be in first position directed away from the nail portion or in a second position in which it overlies a portion of the nail portion. In the first position, the handle is used to insert the plate into the bone, and in the second position the handle is used to drill holes for the cortical screws.

A system is provided for implanting the cortical screws, and includes a screw guide cannula, a drill guide cannula, and an obturator. These three units assembled together form a tapered end that permits them to be inserted through a small skin incision and to dissect the tissue down to the bone. Then the obturator is pulled out and the drill is introduced and used to drill through the cortex. The drill guide is then pulled out and the screw introduced, attached by friction to the driver. The screw guide has a constant inside diameter just big enough for the head of the screw all the way to just shy of the distal end. At the distal end of the screw guide, the diameter is just a bit smaller than the head of the screw. This is achieved by, for example, (i) leaving a small lip (e.g., by machining) in this area so as to create a slight interference relative to the screw head or (ii) by bending in the end, e.g., with or without the help of slits. In accord with the invention, the force required to overcome the interference between the size of the head of the screw and the smaller diameter at the end of the screw guide is sufficiently small so that the screw head can be driven right through the drill guide. Thus, the purpose of this feature is to retain the screw and allow the surgeon to pull out the screw in case the screw is separated from the driver while the screw is inside the cannula.

Additional objects and advantages of the invention will become apparent to those skilled in the art upon reference to the detailed description taken in conjunction with the provided figures.

BRIEF DESCRIPTION OF THE DRAWINGS

FIG. 1 is a top view of a nail plate according to the invention;

FIG. 2 is a side elevation view of a nail plate according to the invention;

FIG. 3 is a top perspective view of a nail plate according to the invention;

FIG. 4 is an enlarged top perspective view of the head portion of the nail plate of the invention;

FIG. 5 is a bottom perspective view of a nail plate according to the invention;

FIG. 6 is an enlarged bottom perspective view of the head portion of the nail plate of the invention;

FIG. 7 is a side elevation view of a implantation jig coupled to the nail plate, with a handle portion of the jig in a first position;

FIG. 10 is a bottom perspective view of the assembly of the implantation jig and the nail plate, with the handle of the jig in the second position;

FIG. 11 is a enlarged bottom perspective view of an assembly of an implantation jig and a head portion of the nail plate;

FIG. 15 is a bottom perspective view of the nail plate, the implantation jig, and fixation pegs coupled to the nail plate;

FIG. 16 is an enlarged bottom perspective view of the head portion of the nail plate, the implantation jig, and fixation pegs coupled to the head portion of the nail plate;

FIG. 19 is a bottom perspective view of the second embodiment of a nail plate according to the invention;

FIG. 20 is an enlarged bottom perspective view of the head portion of the second embodiment of the nail plate;

FIG. 21 is a side elevation view of the second embodiment of the nail plate, shown with the jig and the screw guide cannula;

DETAILED DESCRIPTION

Figure 8:
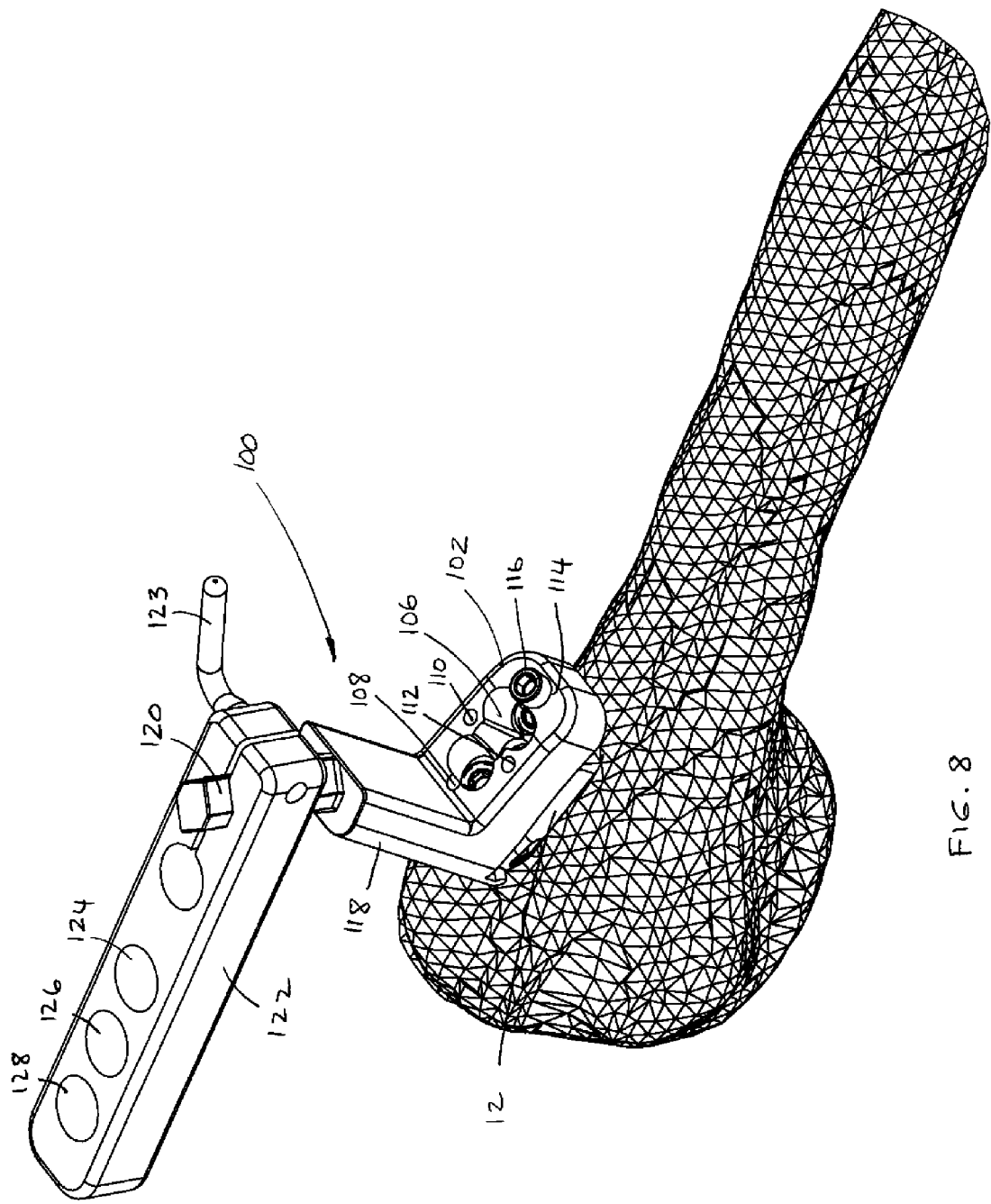
FIG. 8 is a perspective view of the implantation jig coupled to the nail plate, with the handle portion of the jig in the first position.

Nail plates specifically for the fixation of metaphyseal fractures of the distal radius are described in U.S. Pat. Nos. 6,730,090 and 6,706,046, which are hereby incorporated by reference in their entireties herein. The following nail plate is designed for the proximal humerus and includes several novel and significant modifications relative to prior nail plates, as well as a new implantation jig, which are now described.

Referring to FIGS. 1-6, a fracture fixation system is provided and includes a nail plate 10 having a plate-like head portion 12, an intramedullary nail portion 14, and a bent neck portion 16 therebetween which defines an angle α between the head portion 12 and upper surface 17 of the nail portion 14. The angle α is preferably approximately 10°-25° to accommodate the angle between the diaphysis 162 of the humerus 160 and outside of the metaphysis 164 of the proximal humerus. (See also FIGS. 12 and 24.)

Figure 13:
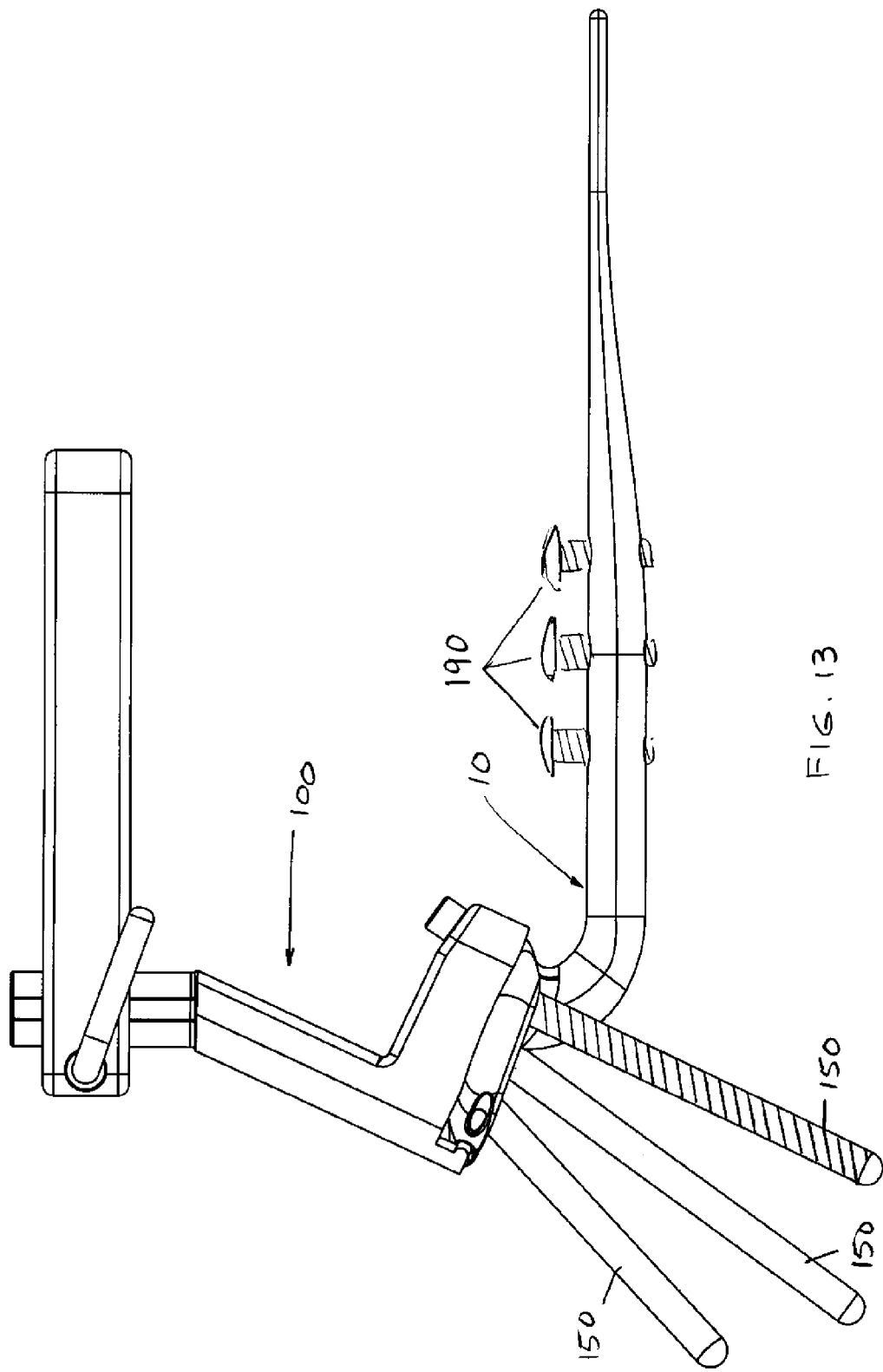
FIG. 13 is a view similar to FIG. 9, but showing fixation pegs coupled to the head portion of the nail plate.
Figure 14:
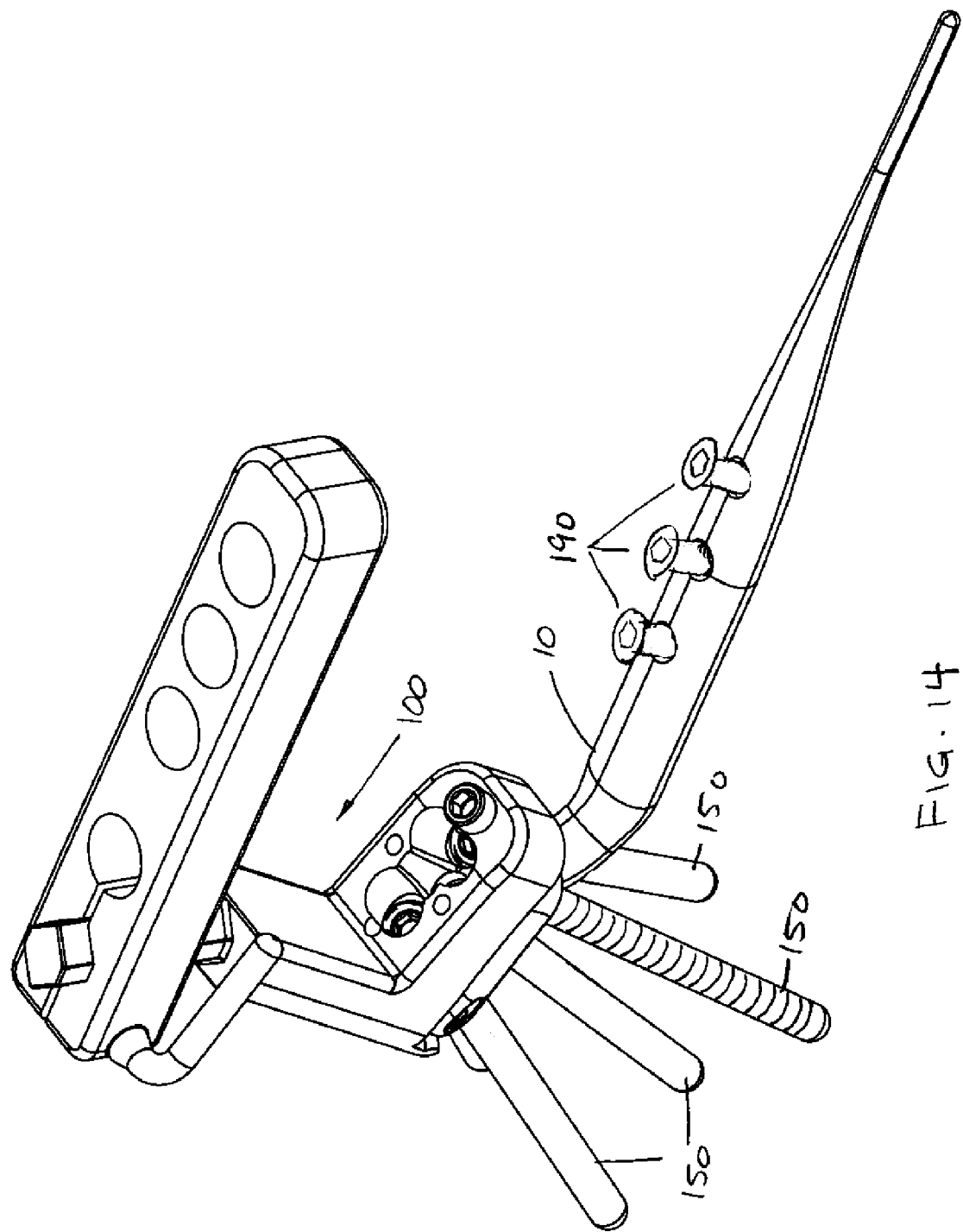
FIG. 14 is a top perspective view of the nail plate, the implantation jig, and fixation pegs coupled to the nail plate.
Figure 17:
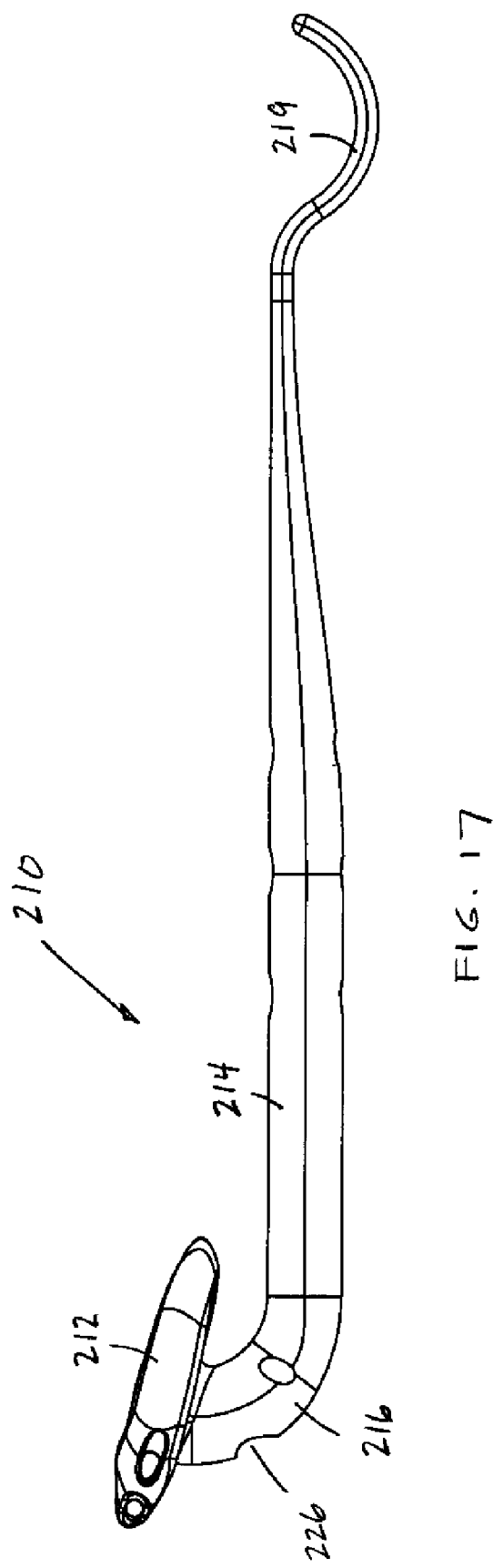
FIG. 17 is a side elevation of a second embodiment of a nail plate according to the invention.
Figure 18:
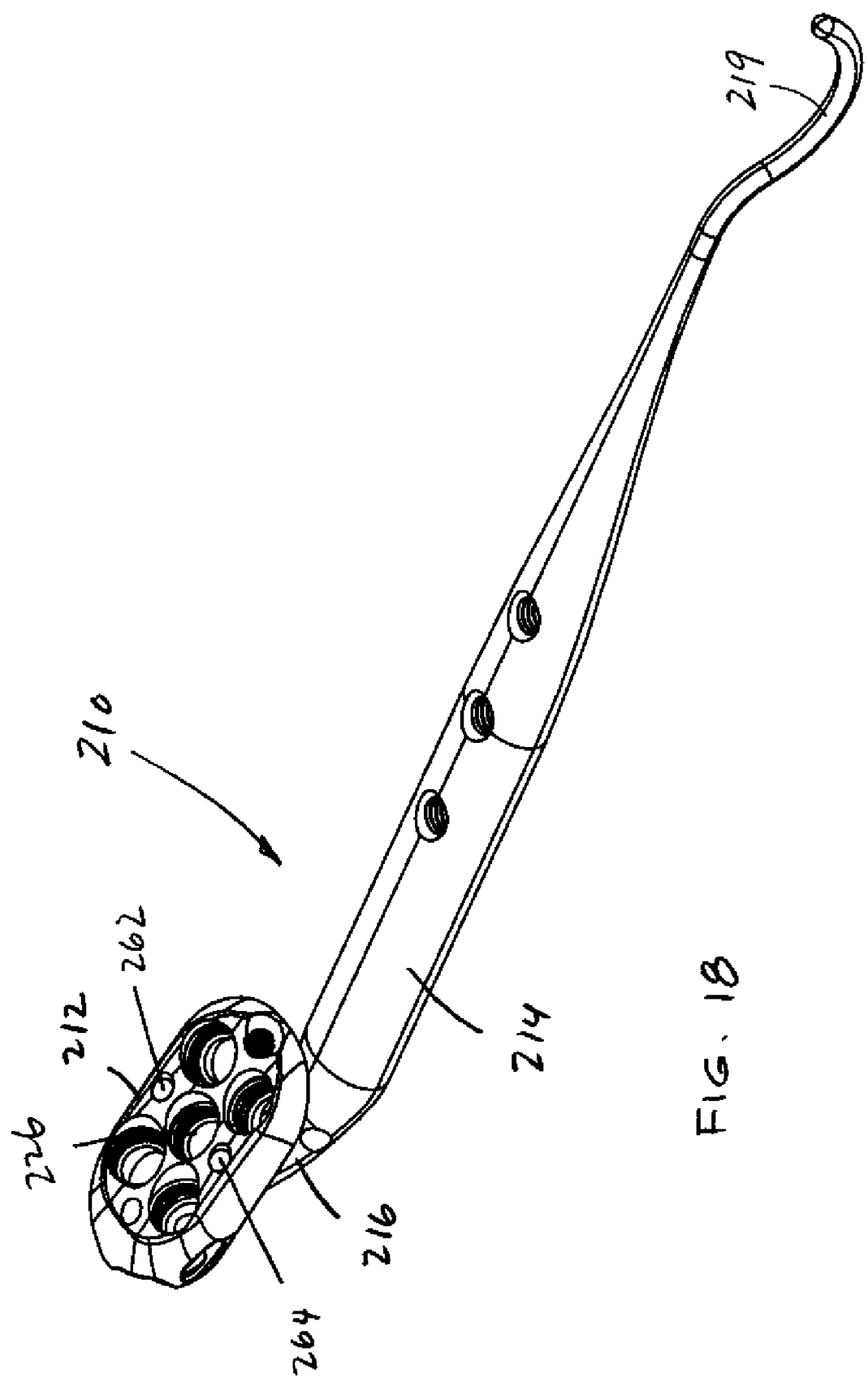
FIG. 18 is a top perspective view of the second embodiment of a nail plate according to the invention.
Figure 25:
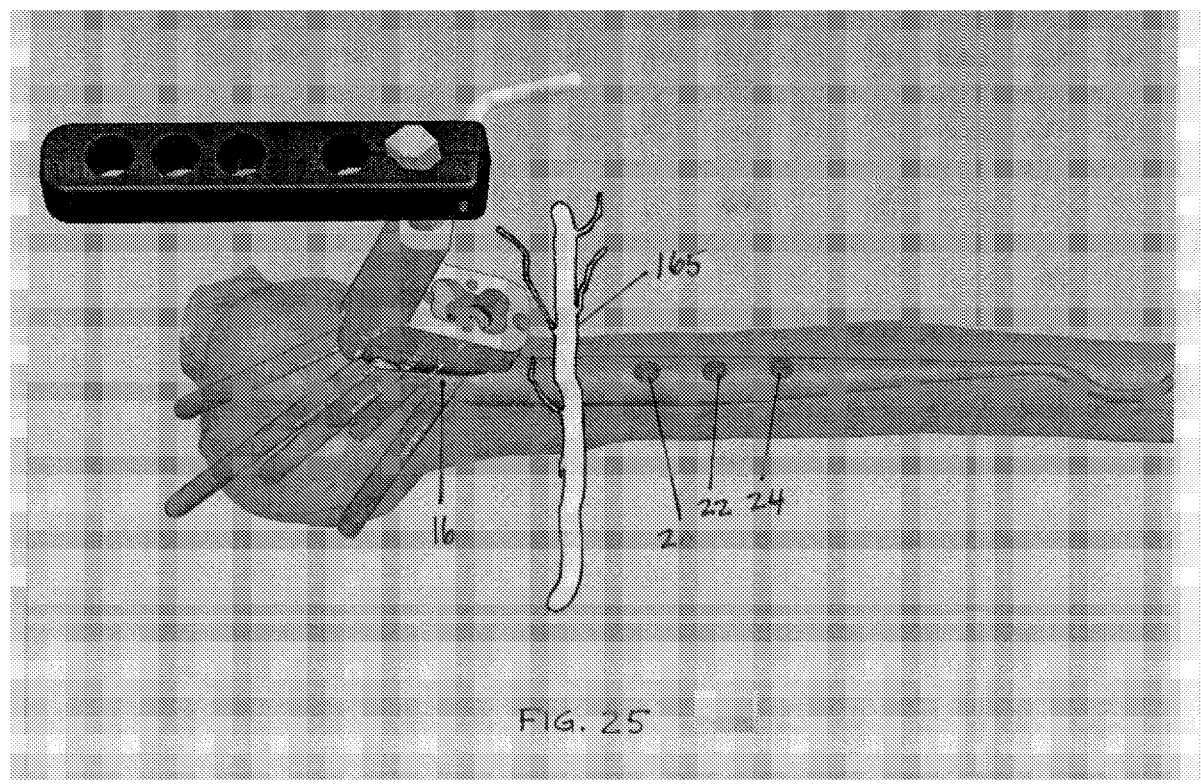
FIG. 25 is a partially transparent view of the nail plate implanted in a humerus bone, the implantation jig coupled to the nail plate, and the axillary nerve running over the humerus bone.

The upper (anatomically lateral) surface 17 of the nail portion 14 defines a substantially straight line for contact with the endosteum of the medullary canal, while a lower (anatomically medial) surface 18 curves or angles to approach the upper surface to cause the nail portion to taper in dimension toward a tail end 19. The tail end 19 has a substantially uniform smaller diameter to facilitate entry into the medullary canal. The nail portion 14 includes three cortical screw holes 20, 22, 24 which preferably are provided with machine threads for receiving the threaded shaft of a preferably unicortical screws with machine threads. Referring to FIGS. 2 and 25, the cortical screw holes 20, 22, 24 are spaced apart from the neck 16 a suitable distance D to prevent screws 190 (FIGS. 13-15) which will be inserted therethrough from interfering with the axillary nerve 165 which runs approximately 5 cm below the acromium. A preferred distance D is approximately 3-4 cm, and more preferably approximately 3.4 cm, from a tangent T to the inside curve of the neck 16 which will seat against the distal side of the fracture.

The head portion 12 includes locking holes 26, 28, 30, 32, 34 for receiving fixed-angle locking pegs 46, 48, 50, 52, 54 or locking screws (FIGS. 13-16), i.e., 'bone support elements'. The locking holes are preferably made 'locking' via the inclusion of internal threads. In a preferred embodiment five locking holes are provided, with the central locking hole 26 defining an axis directed toward the center of the articular surface of the humeral head, and the relatively proximal and distal (and anterior and posterior) locking holes 28, 30, 32, 34 having axes spatially distributed and diverging from the axis of the central locking hole 26 and each other but forming a multiaxial arrangement within the humeral head. The head portion 12 also includes a plurality of K-wire alignment holes 60, 62, 64 which closely receive K-wires and direct such wires to anticipate the placement of the bone support elements. Alignment holes 62, 64 are located on anterior and posterior sides of central hole 26 and have axes which extend parallel to the axis of central hole 26. The use of alignment holes 60, 62, 64 and K-wires in this manner is described in more detail in U.S. Ser. Nos. 10/689,797, filed Oct. 21, 2003, Ser. No. 10/664,371, filed Sep. 17, 2003, and Ser. No. 10/985, 598, filed Nov. 10, 2004, and Ser. No. 11/040,724, filed Jan. 21, 2005, which are hereby incorporated by reference herein in their entireties. The plate also includes a threaded jig hole 66.

The front of the head portion 12 includes tunnel-like suture holes accessible by a curved suture needle. In a preferred embodiment, three tunnels are provided: a first central tunnel 70 perpendicular to a proximal-distal axis $A_1$ of the head portion and extending through the central plane P of the head portion 12, and second and third tunnels 72, 74 on either side of the first 70 which are at an angle of about 45°±15° degrees with respect to the first tunnel. Each tunnel preferably includes a side which is longer than the thickness of the head portion. A catch is defined by two grooves 76 in between the three suture holes 70, 72, 74 or by other suitable structure at the front end of the head portion 12. The grooves 76 also allow a suture needle to enter the tunnels. According to the invention, the upper and front contours of the head portion 12 are devoid of scallops and protrusions such that there is no apparent disruption to the contour of the plate by the suture holes. The advantage of a smooth front end is that it presents no side-to-side resistance to tissue moving across the head portion.

Figure 9:
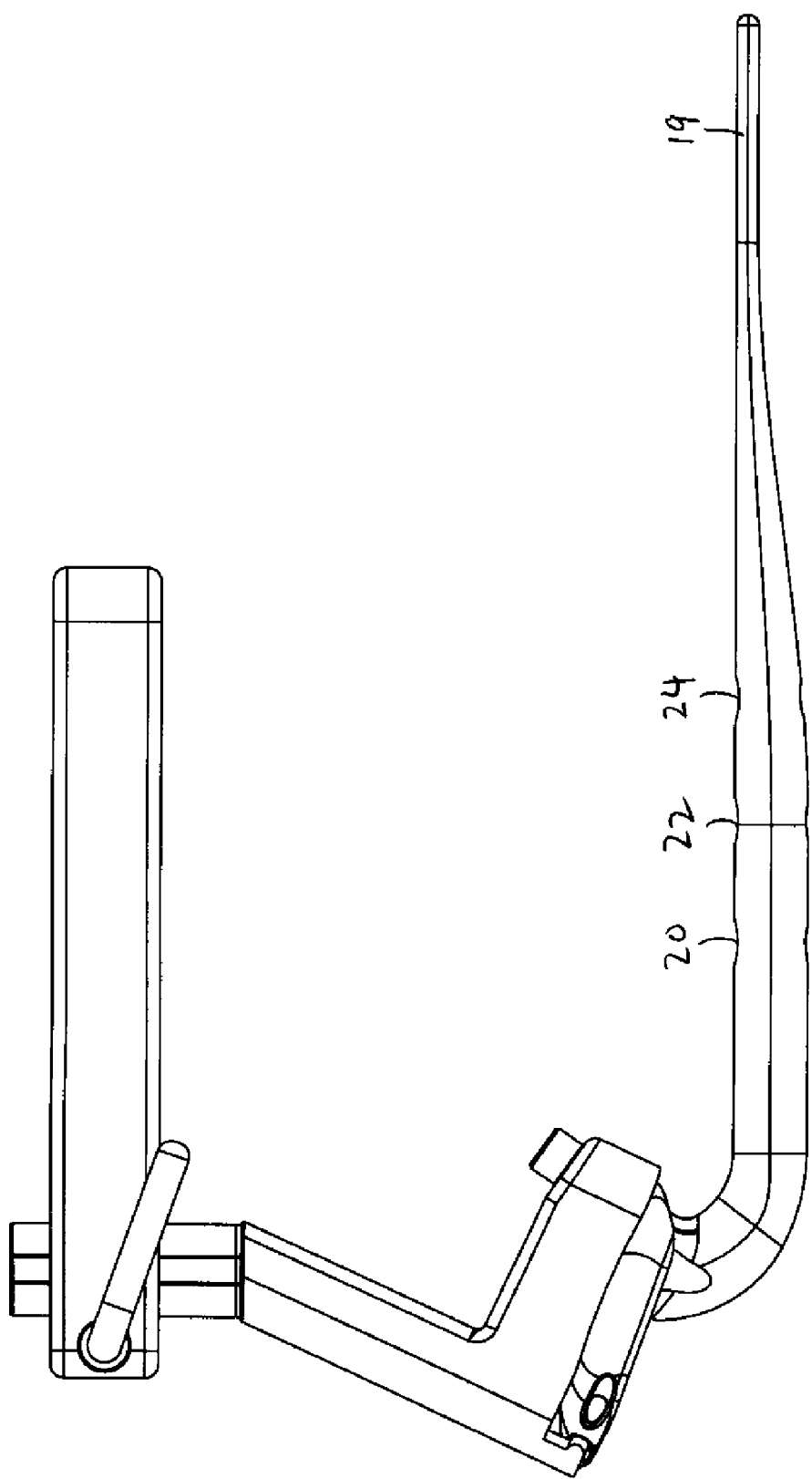
FIG. 9 is a side elevation view of an assembly of an implantation jig and a nail plate, with the handle of the jig in a second position.
Figure 12:
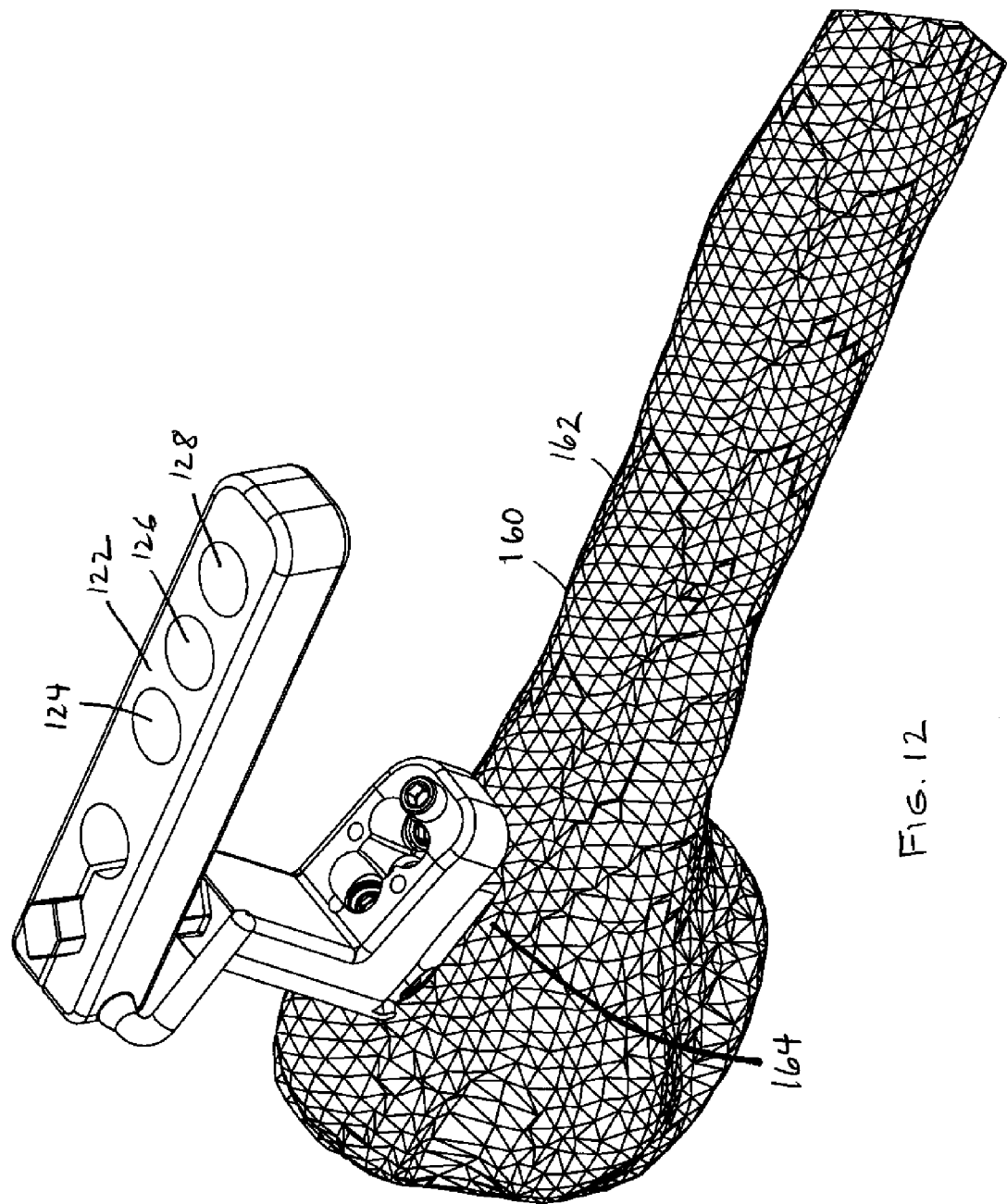
FIG. 12 shows the nail plate implanted in a humerus bone, with the head portion of the nail plate seated on the proximal humerus and the implantation jig coupled to the head portion, a handle portion of the jig overlying the nail portion of the nail plate and providing alignment holes for drilling screw holes through the bone and in alignment with screw holes in the nail portion.

Referring to FIGS. 7-12, an implantation jig 100 is also provided. The jig 100 can be coupled to the device 10, and specifically the head portion 12. The jig includes a base (or foot) 102 with two implant anchors 104, an access opening 106 through which the threaded or non-threaded shaft locking pegs 150 (FIGS. 13-16) may be inserted into the head portion of the device, alignment holes 108, 110, 112 in alignment with K-wire alignment holes 60, 62, 64, and a coupling hole 114. The base 102 is secured to the head portion 12 of the plate by engaging the anchors 104 in the grooves 76 of the catch and securing a screw 116 through the coupling hole 114 and into the jig hole 66. (See also FIG. 11.) A pedestal 118 extends upward from the front of the base 102. A handle mount 120 having at least a portion with a non-circular cross-section is provided at an upper portion of the pedestal 118 and oriented so as to be perpendicular to the upper surface 18 of the nail portion 14 (FIG. 9). A handle 122 is coupled to the non-circular mount 120 via a releasable clamp 123 which permits the handle to be secured in a first position generally opposite the nail portion 14 (FIGS. 7 and 8) or removed and repositioned (reconfigured) into a second position at least partially over the nail portion (FIG. 9). Referring to FIGS. 10 and 12, the handle 122 includes guide holes 124, 126, 128 which when the handle is in the second position overlie the cortical screw holes 20, 22, 24 in the nail portion in the humeral bone 160. The first position is particularly useful during manipulation of the nail portion of the device through the intrafocal space and into the medullary canal, and during insertion of the K-wires through the alignment holes 60, 62, 64 and implantation of the locking screws 150. The second position is used during installation of the cortical screws into the nail portion, as discussed in more detail below.

Figure 22:
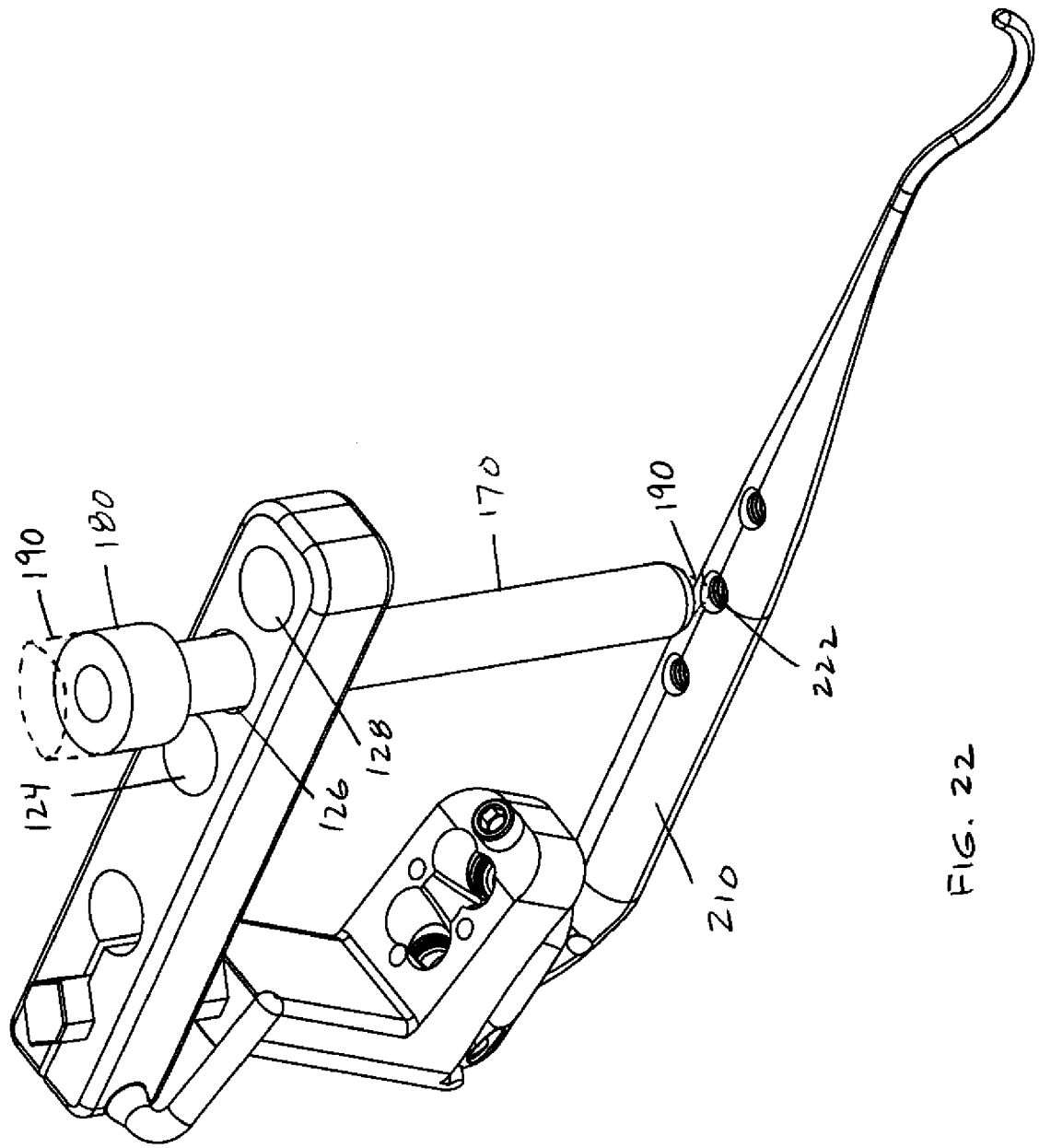
FIG. 22 is a top perspective view of the second embodiment of the nail plate, shown with the jig and the screw guide cannula.
Figure 23:
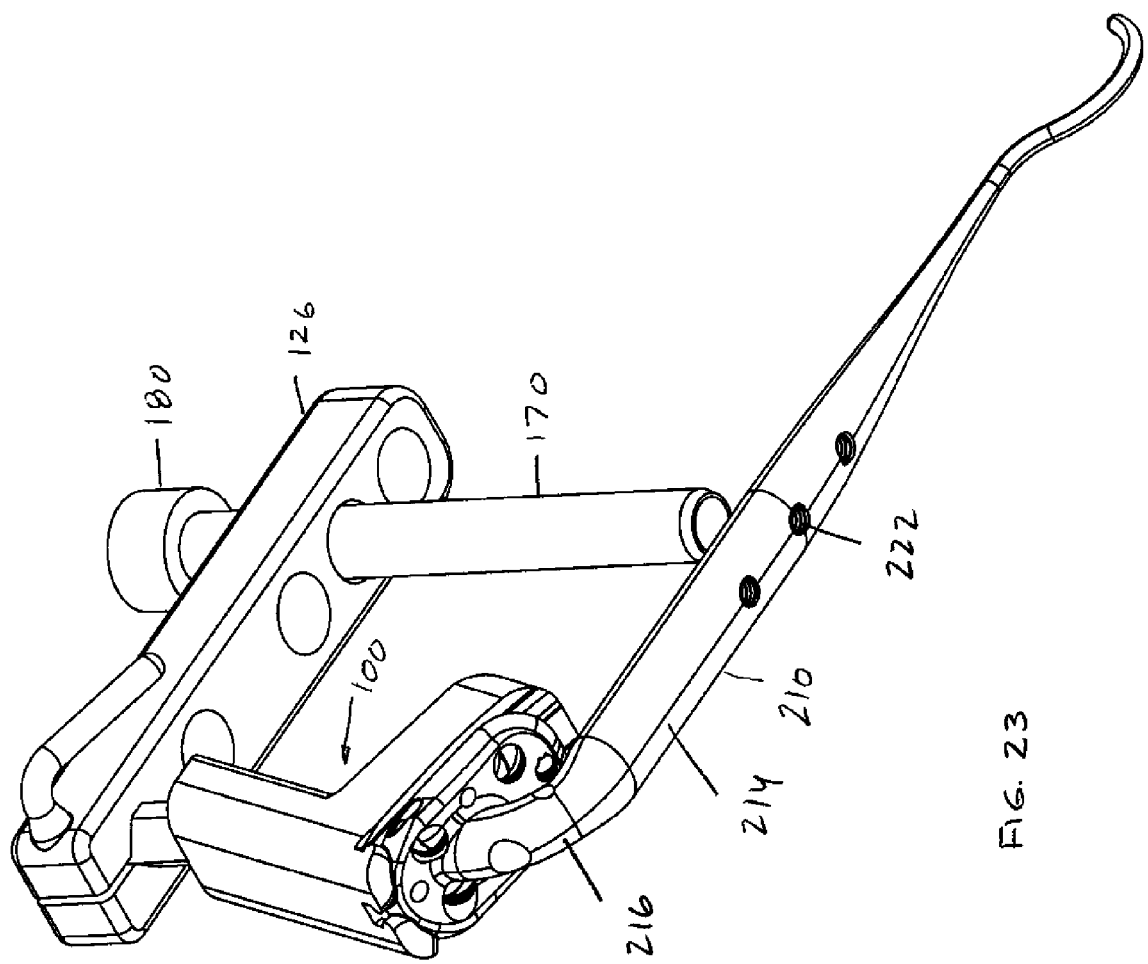
FIG. 23 is a bottom perspective view of the second embodiment of the nail plate, shown with the jig and the screw guide cannula.

A screw guide cannula 170, a drill guide cannula 180, and an obturator 190 are provided for use with the jig 100 (See FIGS. 21-23). These three units assembled together form a tapered end that permits them to be inserted through a small skin incision and to dissect the tissue down to the bone. The assembly is inserted through one of the holes 124, 126, 128 and maneuvered down to the bone. The obturator 190 is then withdrawn and a drill is introduced through the drill guide 180 and used to drill through the bone cortex over one of the holes 20, 22, 24. The drill and drill guide are then pulled out and a machine screw is introduced through the cannula 170, attached by friction to a driver. In accord with one embodiment, the screw guide cannula 170 has a proximal opening (first end), a distant end (second end) and a longitudinally extending central portion therebetween. The central portion has a constant inside diameter just big enough for the head of the screw and extends all the way to just shy of the distal end. At the distal end of the screw guide 170, the diameter is just a bit smaller than the head of the screw. This is achieved by, for example, (i) leaving a small lip (e.g., by machining) in this area so as to create a slight interference relative to the screw head or (ii) by bending in the end, e.g., with or without the help of slits. In accord with the invention, the force required to overcome the interference between the screw head and the smaller diameter at the end of the screw guide 170 is sufficiently small so that the screw head can be driven right through the screw guide and into holes in the nail portion of the device within the bone. Thus, the purpose of this feature is to retain the screw and allow the surgeon to retrieve the screw in the event the screw is separated from the driver while the screw is inside the guide 170.

Figure 28:
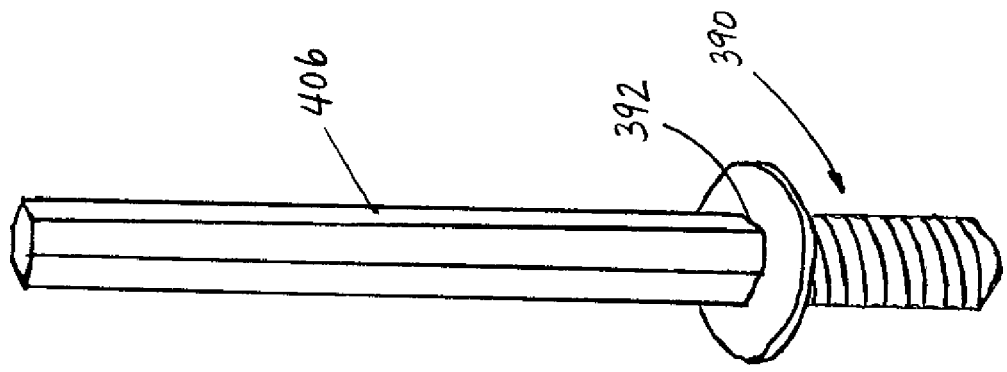
FIG. 28 is a perspective view of a screw driver coupled to a unicortical bone screw.
Figure 27:
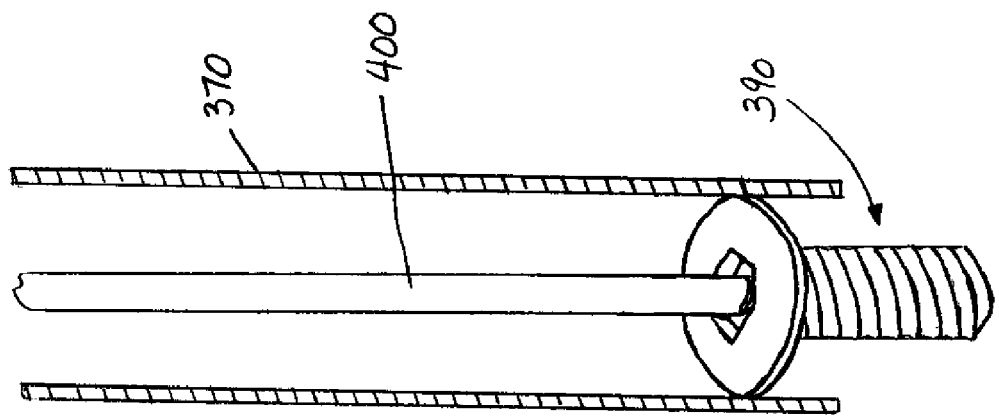
FIG. 27 is a perspective view of a unicortical bone screw and coupling rod for inserting the screw, shown coupled and extending through a screw guide.
Figure 26:
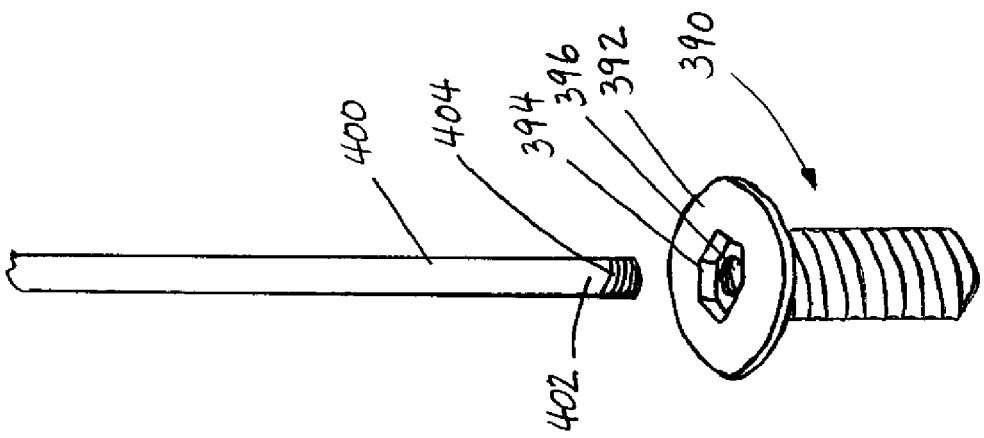
FIG. 26 is a perspective view of a unicortical bone screw and coupling rod for inserting the screw, shown decoupled.

Referring to FIGS. 26-28, an alternative screw capture system to facilitate screw insertion is provided. In this system a standard constant diameter guide 370 (shown in section) is used. The screw 390 include a head 392 including a central hex slot 394 for a driver 406 and a reverse-hand threaded recess 396 (opposite the travel of the machine threads on the shaft of the screw) at the base of the hex slot 394. A coupling rod 400 is provided with an end 402 having a reverse-hand thread 404. As shown in FIG. 27, the rod 400 is physically connected to the screw 390 by a reverse-hand threaded coupling. The rod 400 is then used to maneuver the screw 390 through the guide 370, the hole drilled in the bone, and into a screw hole 20, 22, 24 in the nail portion 14 (FIG. 3). The rod 400 is then rotated to insert the screw 390 into the screw hole, and the rod substantially simultaneously unthreads from the screw head 392 to decouple from the screw. As shown in FIG. 28, a driver 406 is then inserted into the hex slot 394 and driven to complete insertion of the screw 390 into the screw hole. It is also appreciated that the threaded coupling between the screw 390 and rod 400 may be designed to have greater interference inhibiting release between the two. As such, the rod 400 can then be used to substantially completely insert the screw 390 prior to release of the rod, with the driver 406 being used for final screw tightening. It is also appreciated that any conventional screw driving system can be used.

Regardless of exactly how the screw is driven to engage the hole 20, 22, 24 in the nail portion 14 of the device 10, driving the screw into the nail portion causes the nail portion to be pulled against the endosteal surface of the cortex, with the head of the screw seating on the outer surface of the bone. The process is repeated for the other holes 20, 22, 24 to insert unicortical screws 190, 390 with machine threads into the holes to clamp the nail portion 14 against the bone.

Turning now to FIGS. 17-20, a second embodiment of a nail plate 210 according to the invention is shown. The nail plate 210 is substantially similar to nail plate 10, but includes the following distinctions. The head portion 212 is set back relatively further on the neck 216 such that the central locking hole 226 extends through the neck and further clearance is provided between the front end of the head portion 212 and the acromium. Also, the tail end 219 of the nail portion 214 is provided with a downward and then upward curve which facilitates maneuvering the tail end of the nail portion for intrafocal entry.

Referring now to FIGS. 21-23, the nail plate 210 is shown coupled to the implantation jig 100. The implantation jig 100 can be used without modification with both nail plates 10 and 210. A screw guide cannula 170 and drill guide 180 are shown in a hole 126 in the handle 122 situated over screw hole 222 of the nail portion 214 of the device 210.

Figure 24:
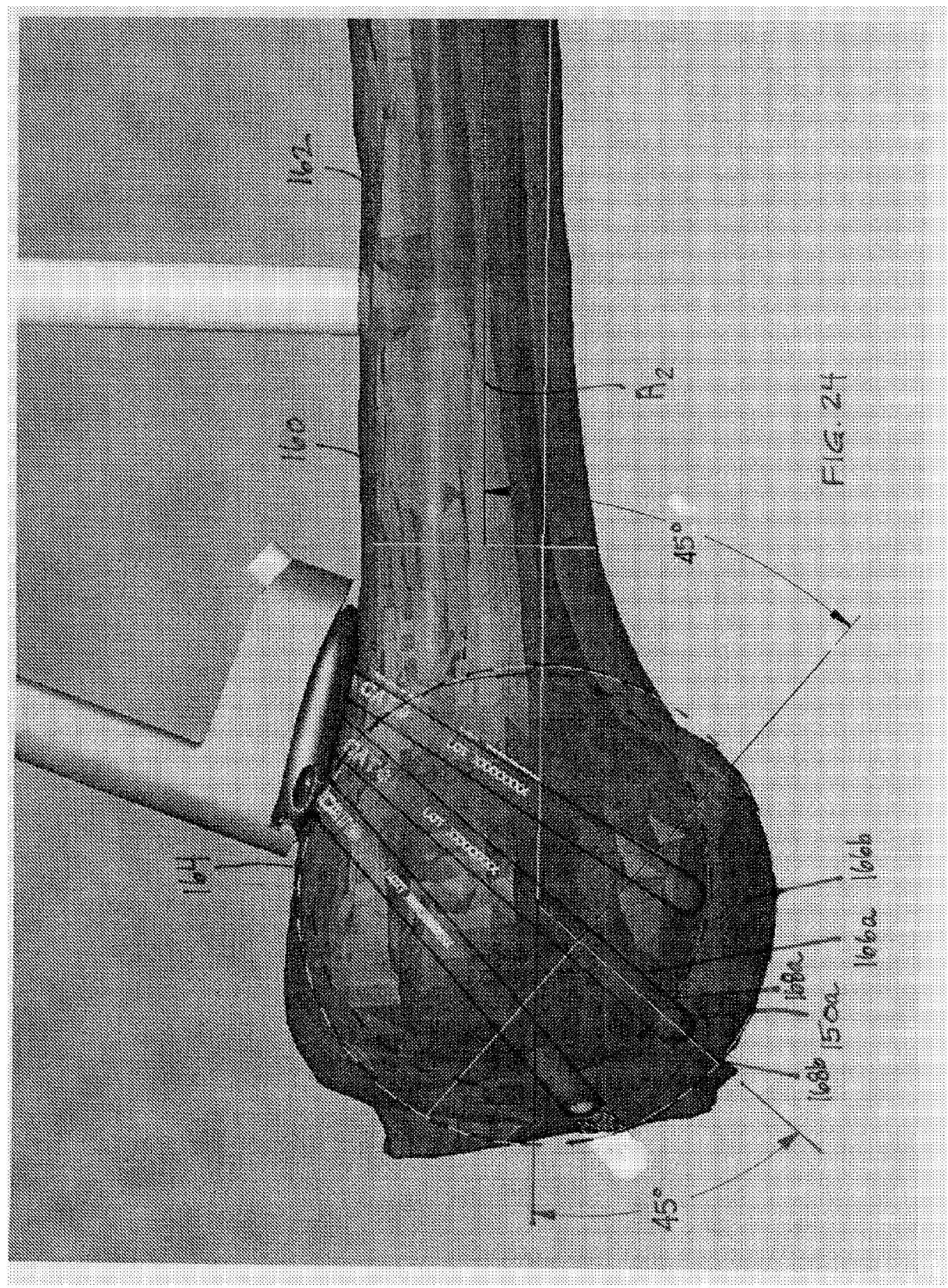
FIG. 24 is a partially transparent view of the nail plate system on a humeral bone with larger and smaller humeral heads indicated as well as landmarks for proper alignment of the nail plate.

Referring to FIG. 24, in accord with the invention, regardless of the size of the humerus bone 160; i.e., whether the head of the bone is relative small as shown at the 166a or relatively large as shown at 166b, a single size implant can be used and the implant can be assured of proper anatomical alignment by extending (i) the nail portion 214 parallel with the axis $A_2$ of the diaphysis 162 and (ii) the central locking peg (or locking screw) 150a toward the center 168a, 168b of the articular surface of the humeral head. Geometrically, the angle between the axis A and a line perpendicular the center of the articular surface is typically 45±20°, and more typically 45°±10°. K-wires (not shown) inserted through alignment holes 262, 264 (FIG. 18) can verify proper alignment of the central hole 226 prior to drilling holes for and inserting the locking peg therethrough. If the central hole is properly aligned, the remaining holes and pegs are assured to be properly spatially distributed.

More particularly, a method of using the nail plate 10 (or 210), jig 100 and cannula 170 is now briefly described. A small incision is made over the fracture down to the bone. A small piece of bone is then removed (using, e.g., a rongeur) on the distal (diaphyseal) side of the fracture to define a space to accommodate the neck 16 of the nail plate 10. The fracture is reduced. The jig 100 is coupled to the nail plate with the handle 122 secured in the first position generally opposite the nail portion 14. The small end 19 of the nail portion 14 is then maneuvered through the incision and intrafocally into the medullary canal until the neck 16 seats within the space defined in the bone and the head portion 12 rests relatively flat on the metaphysis, as shown in FIGS. 7 and 8. Optionally, the nail plate is introduced into the medullary canal and onto the metaphysis manually without attachment to the jig and the jig is later attached.

One or more K-wires are preferably then drilled into the head of the proximal humerus and viewed under fluoroscopy to assure alignment of the head portion over the metaphysis. Assuming the K-wires indicate proper alignment, holes are drilled through the locking holes and into the metaphysis for receiving locking pegs or locking screws. If the K-wire(s) indicate an alignment which is less than desirable, the plate humeral head are relatively realigned, and K-wire(s) are reinserted and reevaluated for alignment and once the alignment is satisfactory, the holes are drilled. The locking pegs 150 or locking screws are inserted into the drilled holes and locked relative to the plate 10 to stabilize the humeral head relative to the head portion 12 of the nail plate.

The handle 122 of the jig 100 is then reversed (or attached) to overlie the nail portion 14 (FIG. 10) and be positioned over the tissue and skin of the upper arm. For each of the guide holes 122, 124, 126, the screw guide cannula 170, drill guide cannula 180 and obturator 190 are together inserted therethrough, with the obturator 190 breaking the skin and defining a path through the tissue to the diaphyseal bone. The obturator 190 is then withdrawn and a drill is introduced through the drill guide 180 and used to drill through the bone cortex over one the respective holes 20, 22, 24. The drill and drill guide are then pulled out and a machine screw attached to a driver is introduced through the cannula 170 and the shaft of the screw is driven into respective hole 20, 22, 24 to cause the nail portion 14 to be drawn against the endosteal surface of the bone. The process is repeated for the remaining holes 20, 22, 24 in the nail portion. The jig 100 is then removed from the nail plate 10 and the incision is closed.

It is recognized that various steps in the method can be interchanged in order without affecting the minimally invasive aspects, efficiency, and fixation provided by the nail plate and the procedure.

Figure 29:
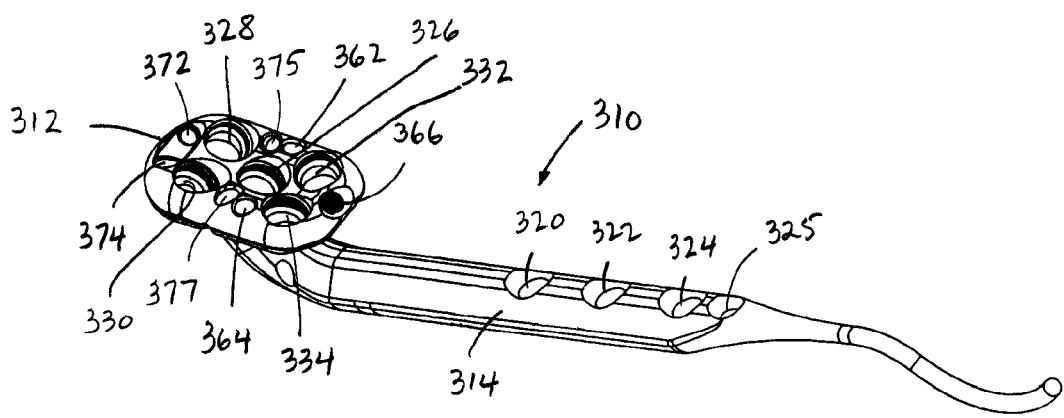
FIG. 29 is a perspective view of a third embodiment of a nail plate according to the invention.

Turning now to FIG. 29, another embodiment of a nail plate 310 is shown. The nail plate 310 includes a head portion 312 having threaded locking holes 326, 328, 330, 332, 334 similar to holes 26, 28, 30, 32, 34 described above. The proximal end of the head portion 312 includes suture holes 372, 374 and the distal end of the head portion includes a threaded jig hole 366. Lateral of the central locking hole 326, cylindrical relatively fixed angle K-wire holes 362, 364 are provided. In addition, adjacent the K-wires holes additional suture holes 375, 377 are provided. The suture holes are configured differently from the K-wire holes in that they are not fixed angle, may have a non-circular shape, and generally have strongly broken or rounded edges to prevent cutting suture material extending therethrough. The nail portion 314 includes threaded holes 320, 322, 324 and a non-threaded cylindrical fixed angle K-wire hole 325 to facilitate alignment and temporary fixation of the nail portion within the medullary canal.

Figure 30:
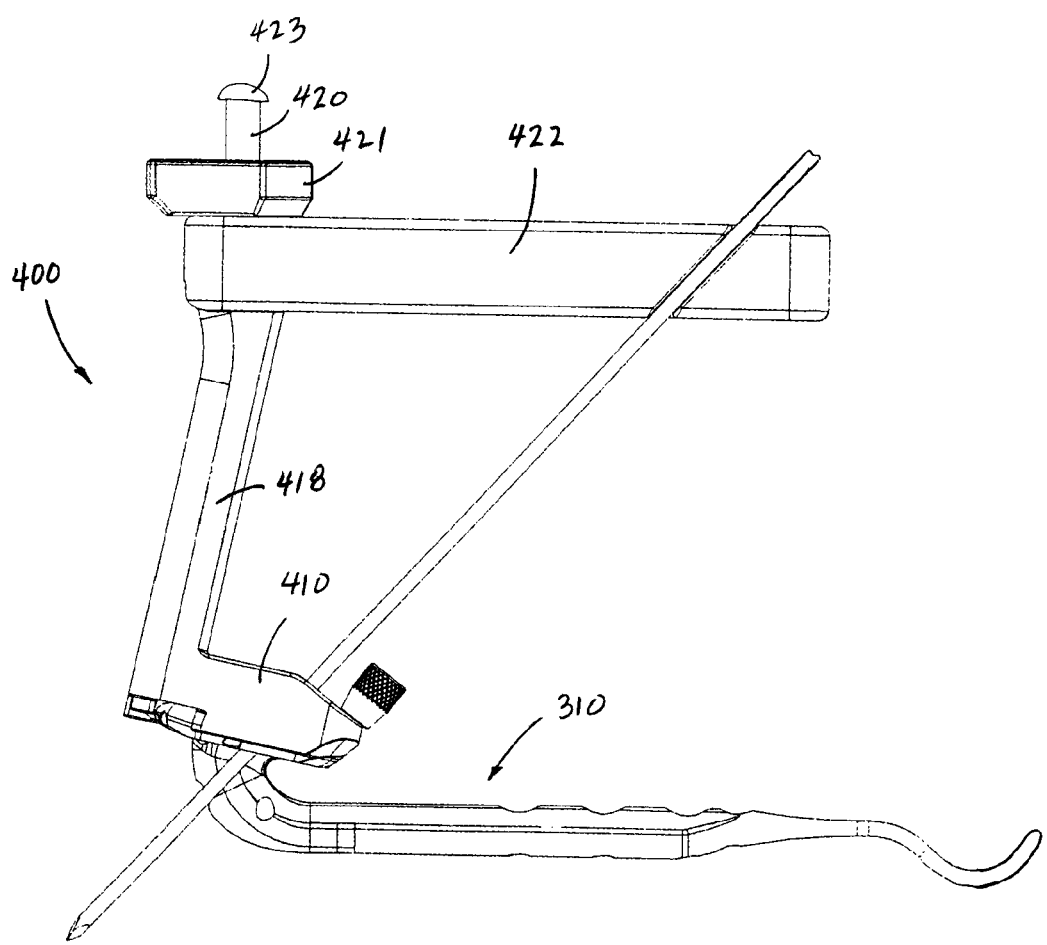
FIG. 30 is a side elevation view of the third embodiment of a nail plate, shown with another embodiment of an implantation jig and K-wires.
Figure 31:
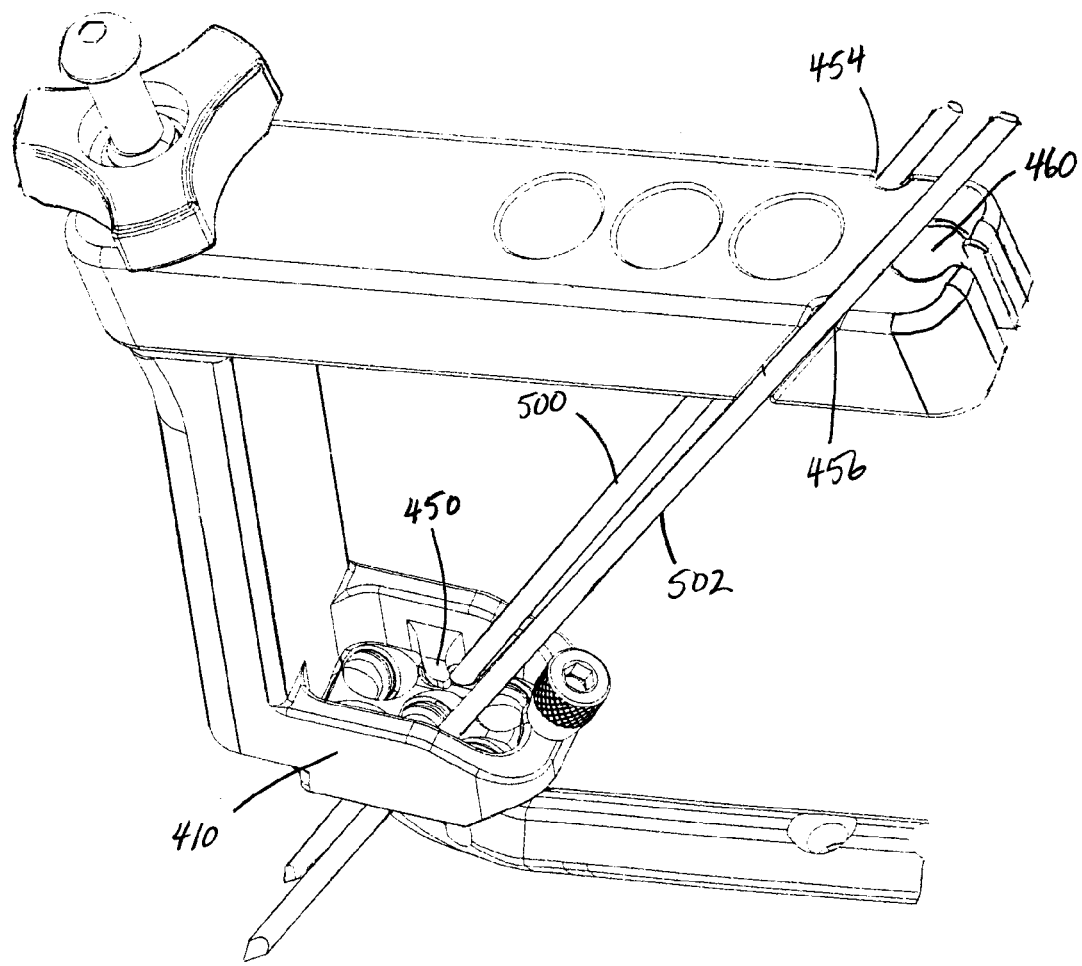
FIG. 31 is a perspective view of the third embodiment of a nail plate, shown with another embodiment of an implantation jig and K-wires.
Figure 32:
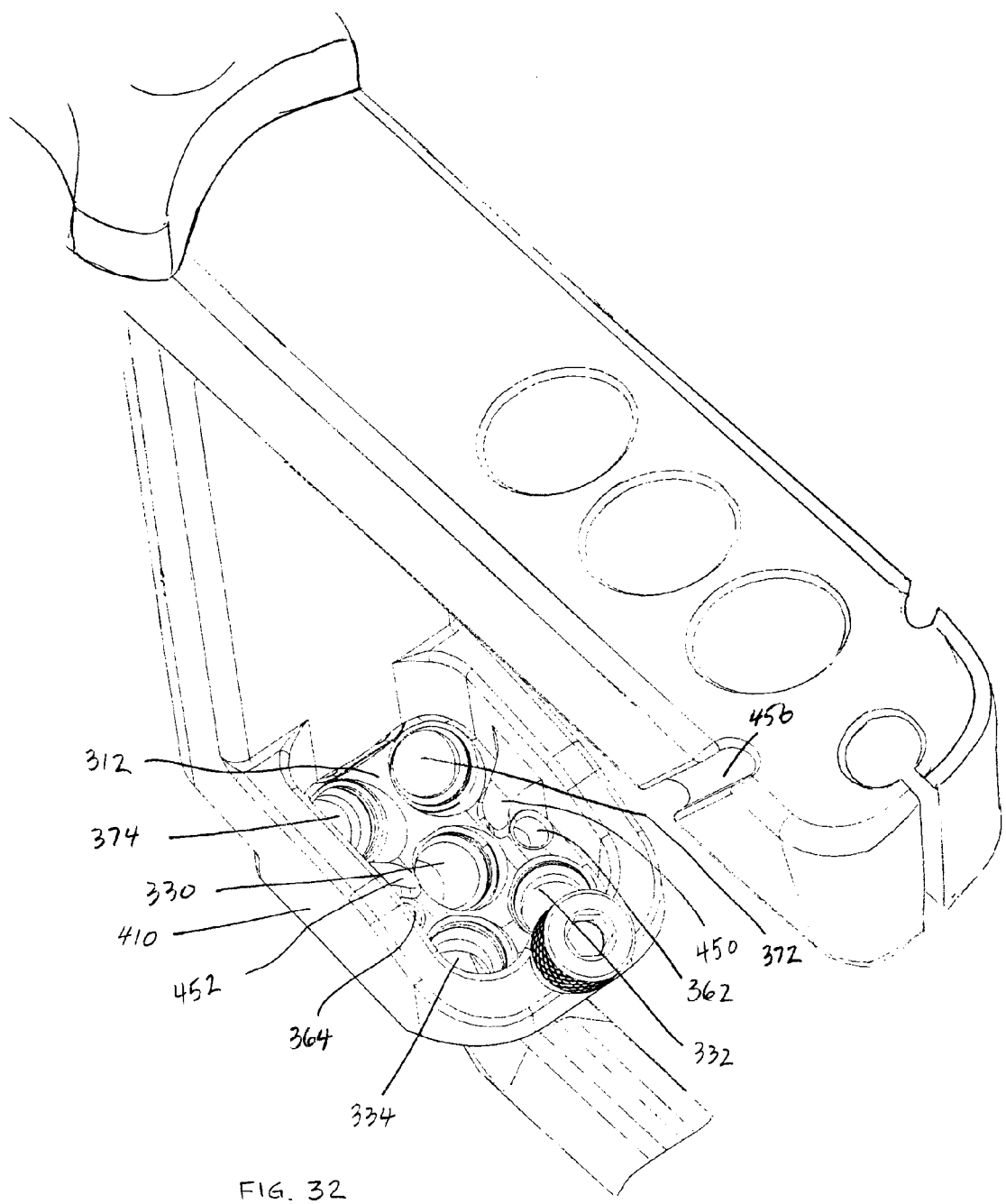
FIG. 32 is an enlarged broken perspective view of the third embodiment of a nail plate shown with the implantation jig.

Referring now to FIGS. 30-32, the nail plate 310 is shown with an implantation jig 400 attached, generally assembled as described above. The jig 400 includes a base (or foot) 410 extending upward into a pedestal 418. The base 410 includes a rim which seats on the periphery of the head portion 412 of the nail plate. The top of the pedestal 418 defines a mount on which a handle portion 422 is rotationally fixed. The handle defines holes for drill guides, as discussed above. The mount is provided with a threaded rod 420, and a locking nut 421 tightens the assembly of the handle 422 to the pedestal 418. The threaded rod 420 includes an enlarged head 423 to prevent the nut from releasing from the assembly.

The jig 400 has certain features to particularly facilitate implantation of the nail plate 310. Referring to FIGS. 29 through 32, during implantation K-wire holes 362, 364 are utilized to confirm proper location of the nail plate prior to inserting locking screws through locking holes 326, 328, 330, 332, 334. It is important that the surgeon that insert or attempt to insert K-wires through adjacent suture holes 375, 377 when making such confirmation for several reasons. First, the suture holes are not fixed angle holes that will provide an indication of the whether the implant is properly oriented within the anatomy. Second, the suture holes are not sized for the K-wire which is used. Thus, it is possible for the K-wire to become lodged in the holes unnecessarily prolonging the procedure. Therefore, the base 410 includes two inwardly extending elements 450, 452 which function as covers for the suture holes 375, 377, but which leave the K-wire holes 362, 364 and locking holes unobstructed 326, 328, 330, 332, 334. Thus, the elements allow access to a specific first type of hole, but block access to a specific different function second type of hole. In addition, the elements are curved and provided adjacent the K-wire holes 362, 364 so as to guide K-wire into the K-wire holes. In addition, to further aid in inserting the K-wires 500, 502 along the proper trajectory into the K-wire holes 362, 364, the handle 422 includes external K-wire slots 454, 456 oriented at an oblique angle relative an axis parallel to the length of the handle aligned to direct K-wires in axial alignment with the K-wire holes 362, 364. The handle 422 also includes a slot or hole 460 to hold a K-wire guide (not shown) to direct a K-wire into the K-wire alignment hole 325 in the nail portion 314 of the nail plate.

There have been described and illustrated herein several embodiments of a fracture fixation system, a jig, and a method of using the jig and implanting the system. While particular embodiments of the invention have been described, it is not intended that the invention be limited thereto, as it is intended that the invention be as broad in scope as the art will allow and that the specification be read likewise. Thus, while the fixation system has been described with respect to the repairing fractures of the humerus, it will be appreciated that the design shown or similar designs with the inventive aspects may be used on other bones, and particularly long bones. It will therefore be appreciated by those skilled in the art that yet other modifications could be made to the provided invention without deviating from its spirit and scope as claimed.

What is claimed is:

1. An implantation jig for use with an orthopedic implant having a plate-like head portion to which fixed angle bone support elements can be coupled and an intramedullary nail portion, comprising:
    a) a base defining an outer rim at which said base is adapted to seat on the implant, a central access opening through said outer rim, and inwardly directed cover elements which obstruct passage through a portion of said access opening;
    b) means for coupling the base to an implant;
    c) a pedestal extending upward from one end of the base; and
    d) a handle coupled relative to the upper portion of the pedestal in a manner which permits the handle to be rotatably secured in a first position generally opposite the nail portion or reconfigured and rotatably secured into a second position at least partially over the nail portion.

2. An implantation jig according to claim 1, wherein:
said cover elements including means for guiding a K-wire into a K-wire hole on the head portion of the implant.

3. An implantation jig according to claim 1, wherein:
the handle includes at least one K-wire alignment means oriented at an oblique angle relative an axis parallel to the length of the handle.

4. An implantation jig according to claim 1, wherein:
the handle includes guide holes which overlie screw holes in the nail portion when the jig is coupled to the implant and the handle is in the second position.

5. An implantation jig according to claim 1, wherein:
the handle mount has a portion with non-circular cross-section, and the handle has a non-circular opening at which it is coupled to the portion of the mount with the non-circular cross-section.

6. An implantation jig according to claim 1, wherein:
the handle is coupled in a rotationally fixed manner under compression.

7. A system of an orthopedic implant and an implantation jig for facilitating implantation of the implant to a fractured bone, comprising:

a) the implant including a plate-like head portion and an intramedullary nail portion, said head portion including first and second types of holes, said first type of hole having a different shape than said first type of hole, said first type of hole is a fixed angle K-wire hole adapted in size and shape to closely receive a K-wire in a fixed angle orientation; and
b) an implantation jig including a base and a handle, said base seats on said head portion of the implant, said base including at least one cover element which obstructs said second type of hole while leaving said first type of hole unobstructed, said base defining a central access portion through which said first type of hole is accessed, and said handle displaced from said base along an axis perpendicular to an axis through said nail portion and including K-wire alignment means which directs a K-wire in axial alignment with said fixed angle K-wire hole.

8. A system according to claim 7, further comprising:
coupling means for coupling the base to the head portion of the implant.

9. A system according to claim 7, wherein:
the second type of hole is a suture hole.

10. A system according to claim 7, wherein:
said cover element includes structure for guiding a K-wire into said first type of hole.

11. A system according to claim 7, wherein:
said head portion further includes locking holes for receiving fixed angle locking screws.

12. A system according to claim 7, wherein:
said jig further includes:
a pedestal extending upward from one end of the base,
wherein the handle is coupled atop the pedestal in a manner which permits the handle to be secured in a first position generally opposite the nail portion and reconfigured into a second position at least partially overlying the nail portion.

13. A system of an orthopedic implant and an implantation jig for facilitating implantation of the implant to a fractured bone, comprising:
    a) the implant including an intramedullary nail portion having a substantially straight endosteal surface and a plurality of screw holes longitudinally displaced along the nail portion, and a plate-like head portion including a first end generally opposite said nail portion and a second end closer to said nail portion, said first end including at least one catch; and
    b) an implantation jig including
        i) a base having at least one anchor which is structured to engage the catch,
        ii) coupling means for coupling the base to the second end of the plate portion of the implant,
        iii) a pedestal extending upward from one end of the base, and
        iv) a handle coupled relative to the handle in a manner which permits the handle to be secured in a first position generally opposite the nail portion and reconfigured into a second position at least partially overlying the nail portion.

* * * * *